United States Patent [19]
Nishikawa et al.

[11] Patent Number: 5,876,714
[45] Date of Patent: Mar. 2, 1999

[54] HUMAN GLYCOSYLTRANSFERASE GENE, COMPOUNDS AND METHOD FOR INHIBITING CANCEROUS METASTASIS

[75] Inventors: Atsushi Nishikawa, Toyonaka; Yoshito Ihara, Mino; Masafumi Yoshimura, Osaka; Shunichiro Taniguchi, Munakata-gun; Naoyuki Taniguchi, Toyonaka, all of Japan

[73] Assignee: Takara Shuzo Co., Ltd., Kyoto-Fu, Japan

[21] Appl. No.: 975,114

[22] Filed: Nov. 20, 1997

Related U.S. Application Data

[60] Division of Ser. No. 524,828, Sep. 7, 1995, which is a continuation-in-part of Ser. No. 107,173, Aug. 17, 1993, abandoned.

[30] Foreign Application Priority Data

Aug. 21, 1992 [JP] Japan .................................. 4-243984
Oct. 12, 1994 [JP] Japan .................................. 6-271802

[51] Int. Cl.$^6$ .............................. A61K 38/45; C12N 9/10
[52] U.S. Cl. ................... 424/94.5; 435/193; 435/252.3; 435/252.33; 435/320.1; 536/23.2; 536/23.5
[58] Field of Search .................... 435/193, 252.3, 435/252.33, 325, 320.1, 365; 536/23.2, 23.5; 424/94.5

[56] References Cited

FOREIGN PATENT DOCUMENTS

WO92/09694  6/1992  WIPO .

OTHER PUBLICATIONS

Y. Ihara et al., *J. Biochem.*, 113(6), 692–698 (Jun. 1993).
A. Nishikawa et al., *J. Biol. Chem.*, 267(25), 18199–18204 (Sep. 1992).
H. Nakao et al., *Biochem. Biophys. Res. Commun.*, 172(3), 1260–1266 (Nov. 15, 1990).
K. Ishibashi et al., *Clin. Chim. Acta*, 185(3), 325–322 (Dec. 15, 1989).
A. Nishikawa et al., *Anal. Biochem.*, 170(2), 349–354 (1988).

*Primary Examiner*—Robert A. Wax
*Assistant Examiner*—Nashaat T. Nashed
*Attorney, Agent, or Firm*—Wenderoth, Lind, & Ponack, L.L.P.

[57] ABSTRACT

A gene encoding human glycosyltransferase (human GnT-III) and recombinant DNA method for producing the enzyme are provided. A cancerous metastasis inhibitor comprising GnT-III, or a gene thereof, and a method of inhibiting cancerous metastasis in a mammal are also provided.

3 Claims, 7 Drawing Sheets

HUMAN GLYCOSYLTRANSFERASE GENE, COMPOUNDS AND METHOD FOR INHIBITING CANCEROUS METASTASIS

REFERENCE TO RELATED APPLICATIONS

This is a divisional of U.S. application Ser. No. 08/524,828, which was filed on Sep. 7, 1995, which is a continuation-in-part of U.S. application Ser. No. 08/107,173, which was filed on Aug. 17, 1993, now abandoned.

BACKGROUND OF THE INVENTION

1. Field of the Invention

This invention relates to a human glycosyltransferase gene and a process for producing the transferase which is useful in the field of sugar engineering. This invention also relates to a drug by which the activity of a specific enzyme in cancer cells or nearby tissues is increased, thereby inhibiting metastasis of the cancer.

2. Description of the Related Art

UDP-N-acetylglucosamine:β-D-mannoside β1-4N-acetyl-glucosaminyltransferase III (EC 2.4.1.144: hereinafter referred to simply as GnT-III), which is an enzyme that transfers a GlcNAc residue in UDP-N-acetylglucosamine (UDP-GlcNAc) to a mannose (Man) residue forming a β1-4 bond in an asparagine binding type sugar chain, was reported for the first time by Narasimhan [see Journal of Biological chemistry, 257, 10235–10242 (1982)]. The GlcNAc transferred by GnT-III, which is called a bisecting GlcNAc, has been found in the sugar chains of various glycoproteins. It has been further reported by Narasimhan et al. [see J. Biol. Chem., 263, 1273–1282 (1988)] and Pascale et al. [see Carcinogenesis, 10, 961–964 (1989)] that the activity of GnT-III increases in rat liver accompanying its canceration.

In addition, Ishibashi et al. have reported an increase in the activity of GnT-III in the serum of a human patient with hepatic cancer [see Clinica Chimica Acta, 185, 325–332 (1989)].

Regarding genes, furthermore, a gene coding for GnT-III originating in rat (rat GnT-III) has been isolated by one of the present inventors [see Japanese Patent Application No. 69345/1992]. It is believed that metastasis is the main problem in clinical medicine for cancer. Namely, metastasis means a phenomenon where cancer cells from a primary tumor enter into the blood system or the lymphatic system and form a new tumor in another part of the body via such a system. If cancer cells do not metastasize or the cancerous metastasis can be prevented, a patient with cancer can be saved by excising the cancer.

It has been clarified that, in many solid cancers, sugar chain structures expressed on the surfaces of cancer cells vary as the cancer advances, i.e., depending on the stage of the advance and the occurrence of the metastatic character. It is therefore considered that the sugar chain structures on the surface of the cancer cells vary as the cancer advances and acquire metastatic character. In particular, it has been widely known that a cell having a sugar chain with a specific branched structure expressed thereon has a potent ability to metastasize as reported by Dennis et al. [Science, 236, 582–585 (1987)]. The evidence thereof is as follows:

1) A leukoagglutinin originating in kidney bean (L-PHA) recognizes an asparagine linked sugar chain having a Galβ1-4GlcNAcβ1-6(Galβ1-4GlcNAcβ1-2)-Manα1 branched structure and binds thereto. A mouse cancer cell line MDAY-D2, which shows a sensitivity to this L-PHA, has metastatic potential. On the other hand, a cell line showing a resistance to L-PHA has low metastatic potential.

2) An L-PHA binding type glycoprotein is detected from the cell membrane of a metastatic cell line, while no L-PHA binding type glycoprotein is detected from the cell membrane of a cell line having low metastatic potential. The incidence of the metastasis correlates to the occurrence of the L-PHA binding type glycoprotein.

3) When an oncogene is introduced into rat cells, the L-PHA binding type glycoprotein appears therein. When these cells are injected into a nude mouse, a tumor is formed and metastasizes.

The results of tissue staining with L-PHA indicate that the L-PHA binding type sugar chain appears not only in cancer cells which have been experimentally formed but also in human breast cancer and colon cancer and that the intensity of the L-PHA staining is elevated as the cancer advances [Cancer Research, 51, 718–723 (1991)].

Since a sugar chain is not a direct product of a gene, a change in the sugar chain structure depends on a glycosyltransferase. It has been reported that a mouse cell line having the L-PHA binding type sugar chain expressed thereon and showing metastatic potential has a higher activity of N-acetyl-glucosaminyltransferase (GnT) V (hereinafter referred to simply as GnT-V), which forms GlcNAcβ1-6Manα1 branching, than a cell line showing low metastatic potential [Science, 236, 582–585 (1987)]. Also, the intensity of L-PHA staining positively correlates to the GnT-V activity in a human breast cancer tissue [Cancer Research, 49, 945–950 (1989)].

As described above, there have been detailed studies on the relationship between the appearance of the L-PHA binding type sugar chain having the GlcNAcβ1-6Manα1-branched structure and the metastatic character of cancer cells. However it has not been revealed so far whether or not the sugar chain on the surface of the cell having such a structure specifies the extent of the advance of the cancer and directly causes the acquisition of the metastatic character. Needless to say, there has been developed neither a method nor a drug whereby the possibility of cancerous metastasis can be effectively reduced.

In the process of the studies relating to structural changes in sugar chains on the surface of cells, the present inventors have successfully acquired rat and human GnT-III genes (Japanese Patent Laid-Open No. 38767/1994 and U.S. patent appln. Ser. No. 08/107,173). This enzyme forms the GlcNAcβ1-4Manβ1 structure of an asparagine linked sugar chain, i.e., the so-called bisecting GlcNAc. It has been reported that the activity of this GnT-III also increases in cancer cells. In particular, the present inventors have clarified that the activity of this enzyme increases in rat or human liver cancer tissues or the serum of a patient with liver cancer [Biochemical and Biophysical Research Communications, 152, 107–112 (1988); and Clinica Chimica Acta, 185, 325–332 (1989)]. Regarding cancers other than liver cancer, it has also been reported that GnT-V and GnT-III activities increase in cells which have been malignantly transformed by introducing N-ras protooncogene thereinto [Journal of Biological Chemistry, 266, 21674–21680 (1991)] and that GnT-III activity largely increases in metastatic prostatic cancer cells [FEBS Letters, 308, 46–49 (1992)].

As described above, GnT-III plays an important role in vivo and is a highly useful enzyme in the diagnosis of cancer because its activity increases accompanying canceration. However reports on human GnT-III have been limited to the determination of its activity and there has been no report of isolation of a human GnT-III gene so far.

The present invention aims to isolate a human GnT-III gene and provide a genetic engineering process for producing human GnT-III.

As described above, it is known that a sugar chain structure on the surface of cancer cells is changed or a glycosyltransferase in cancer cells is activated as the cancer advances or acquires the metastatic character. However, there has been developed no cancerous metastasis inhibitor with the use of these phenomena as the site of action.

It is a further object of the present invention to provide a drug for inhibiting cancerous metastasis by increasing the activity of a specific glycosyltransferase in cancer cells or nearby tissues.

SUMMARY OF THE INVENTION

The present invention can be summarized as follows. The present invention relates to a human glycosyltransferase gene. The present invention also relates to a process for producing a human glycosyltransferase.

The present inventors have prepared a probe from a rat GnT-III gene, screened a human cDNA library for clones containing a gene coding for human GnT-III by using this probe, and succeeded in the isolation of the gene coding for human GnT-III and the expression of human GnT-III with the use of this gene.

The present invention also relates to a cancerous metastasis inhibitor which comprises GnT-III or its gene as the active ingredient.

The present inventors have conducted extensive studies on the relationship between the metastatic character of cancer cells and a change in the sugar chain structure on the surface of the cells. As a result, they have surprisingly found that the ability of cancer cells to metastasize can be unexpectedly inhibited by introducing GnT-III, which is expressed specifically in cancer cells and the activity of which has been considered as rather positively correlating to the extent of the advance of cancer into cancer cells, thus completing the present invention.

The invention will now be described in more detail, with reference to the following examples and drawings.

DETAILED DESCRIPTION OF THE INVENTION

Examples of the probe which can be used in the detection of a gene coding for human GnT-III include a DNA fragment of approximately 1.4 kb which is obtained by cleaving a plasmid SV3 containing the rat GnT-III gene described in the Japanese Patent Application No. 69345/1992 with a restriction enzyme HindIII. The plasmid SV3 can be prepared from *Escherichia coli* XL1-Blue SV3 (FERM BP-4325) which has been deposited with Fermentation Research Institute, Agency of Industrial Science and Technology. By using this DNA fragment as a probe, for example, a commercially available human cDNA library can be screened for a gene coding for human GnT-III by plaque hybridization. As a result of the screening, two positive clones were obtained from $3 \times 10^6$ plaques and respectively named H2 and H3. These clones were digested with EcoRI and then subcloned into, for example, the EcoRI site of Bluescript IISK+ (Stratagene). These subcloned plasmids were named respectively pBluescript II (H2) and pBluescript II (H3).

Figure 2:
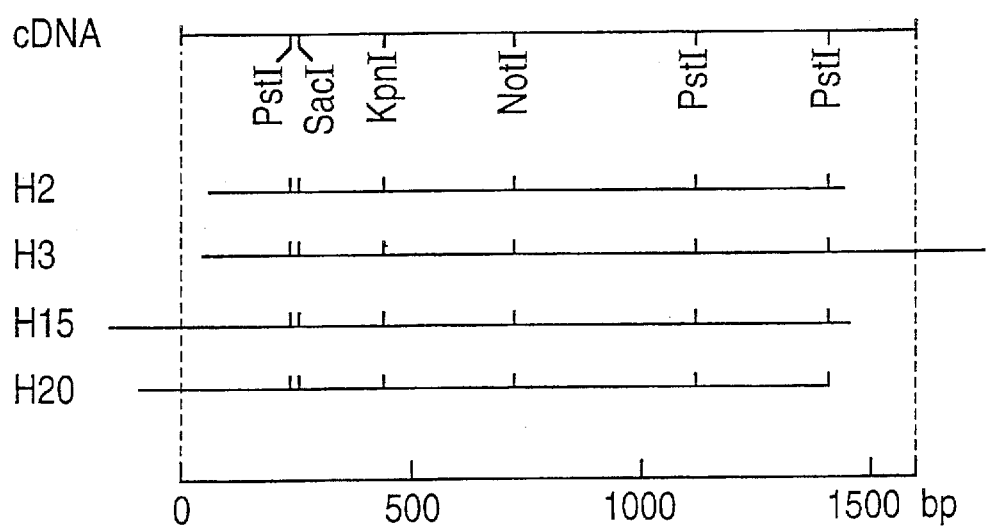
FIG. 2 shows the relationships among four DNAs H2, H3, H15 and H20.

FIG. 2 shows a relationship between H2 and H3 revealed by analyzing with restriction enzymes. Examination of the base sequences of the H2 and H3 plasmids reveals that no initiator codon ATG is involved therein. In order to obtain a full-length gene coding for human GnT-III, therefore, screening of the human cDNA library is effected again with the use of H2 and H3 as a probe. As a result, four positive clones were obtained from $7 \times 10^5$ plaques. These clones were digested with EcoRI and then subcloned into, for example, the EcoRI site of Bluescript IISK+.

From among the subcloned DNAs, two DNAs containing an initiator codon are named respectively H15 and H20. The plasmids having H15 and H20 subcloned therein are named respectively pBluescript II (H15) and pBluescript II (H20). FIG. 2 shows a relationship between H15 and H20 revealed by analyzing with restriction enzymes.

Figure 3:
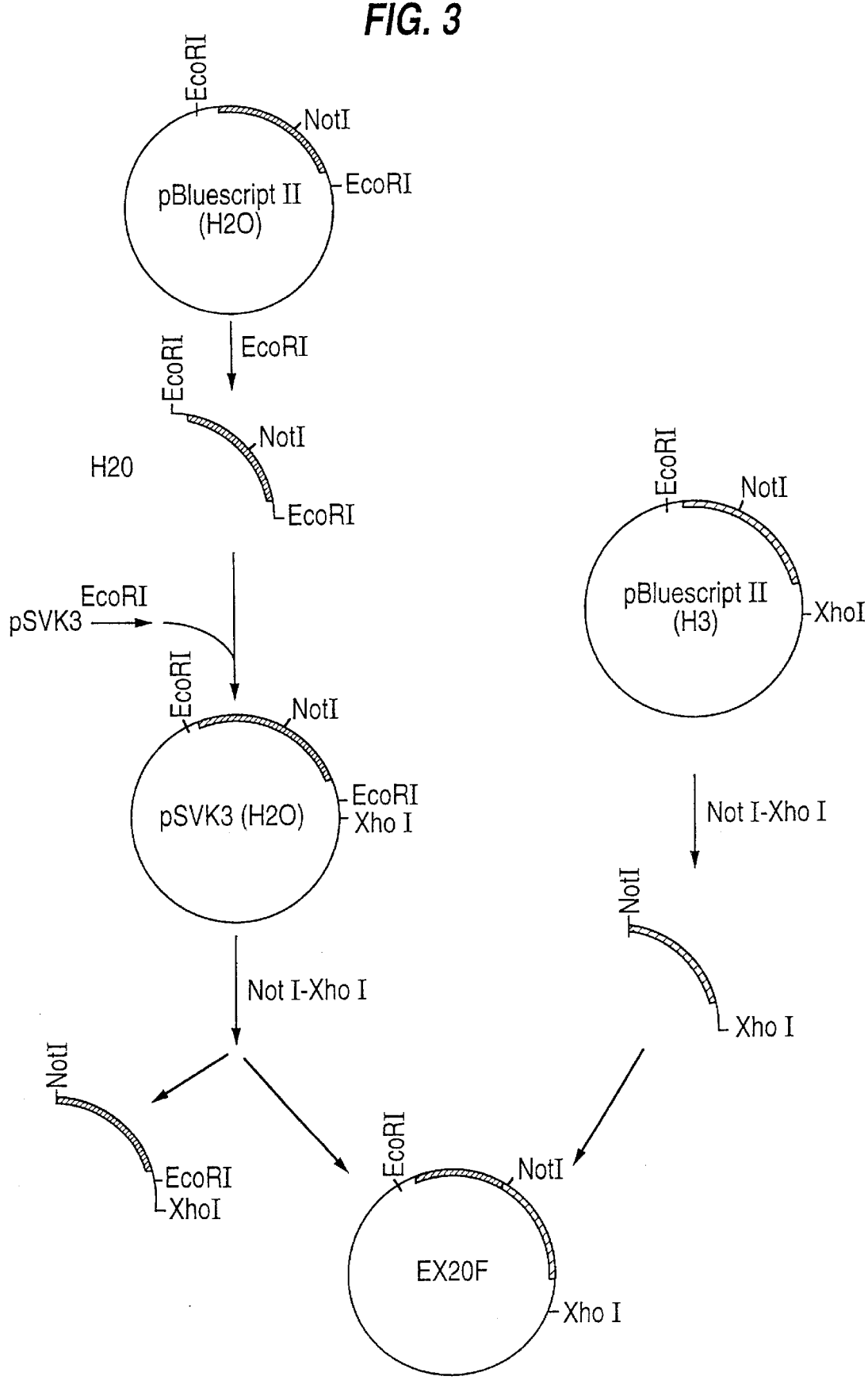
FIG. 3 depicts the construction of plasmid EX20F.

Next, an expression plasmid containing a full-length human GnT-III gene can be constructed by, for example, excising H20 from pBluescript II (H20) with ECORI and integrating it into pSVK3 (Pharmacia) to prepare pSVK (H20). Further, a fragment excised from pBluescript II (H3) having H3 integrated thereinto with NotI and XhoI is integrated into the pSVK(H20) in such a manner as to replace the NotI-XhoI fragment of the pSVK(H20) therewith, thus constructing an expression plasmid EX20F (see FIG. 3).

Figure 1:
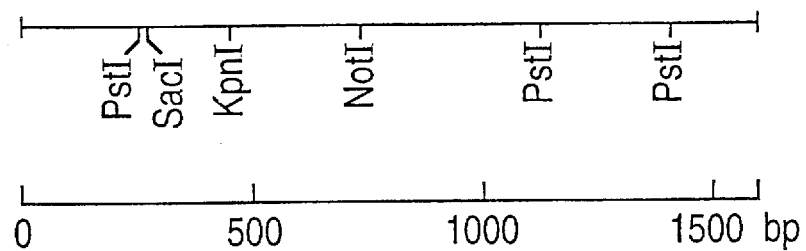
FIG. 1 shows a restriction map of a gene coding for human GnT-III.

The base sequence of the DNA fragment integrated into EX20F can be determined by the dideoxy method. SEQ ID NO. 1 in the sequence listing shows a part of the base sequence thus determined. As the result of screening of an open reading frame (ORF), an ORF is found in bases Nos. 169 to 1761. FIG. 1 shows a restriction map of this ORF region. SEQ ID NO. 2 in the sequence listing shows the nucleic acid sequence and SEQ ID NO. 4 shows the deduced amino acid sequence of the ORF region.

Human GnT-III producing cells can be obtained by transforming expression cells by an expression plasmid and examining the capability of the transformant to express human GnT-III. Examples of usable expression cells include COS-1 cells (ATCC CRL 1650). For example, the COS-1 cells can be transformed by the above expression plasmid EX20F. Then the transformant is incubated and the activity of GnT-III expressed in the transformant is determined to specify a gene coding for human GnT-III. This gene is integrated into EX20F and a part of its base sequence is located on a DNA fragment represented by SEQ ID NO. 1. Human GnT-III can be produced by genetic engineering technique by incubating the above transformant.

By effecting hybridization with the use of the gene thus obtained as a probe under stringent conditions, it is anticipated that genes for enzymes analogous to that of the present invention, which are different therefrom in sequence but expected to have a similar activity, may be obtained. The term "under stringent conditions" as used herein means that the hybridization of a nylon membrane having DNAs immobilized thereon with the probe is conducted in a solution containing 6×SSC (1×SSC means a solution prepared by dissolving 8.76 g of sodium chloride and 4.41 g of sodium citrate in 1 liter of water), 1% of sodium lauryl sulfate, 100 μg/ml of salmon sperm DNA, and 5×Denhardt's (containing bovine serum albumin, polyvinylpyrrolidone and Ficoll each at a concentration of 0.1%) at 65° C. for 20 hours.

As described above in detail, the present invention enables a gene coding for human GnT-III to be isolated and provides a process for producing human GnT-III by using the gene. This gene and its decomposition products are usable in the determination of human GnT-III during the expression process in vivo and, therefore, are useful in the genetic diagnosis of cancer, and so forth. In addition, various antibodies can be immunologically prepared by using polypeptides coded for by the gene of the present invention. These antibodies are also useful in the field of diagnosis and for the purification of human GnT-III.

In the present invention, the object of inhibiting cancer metastasis can be achieved by introducing GnT-III into cancer cells or the tissues therearound. GnT-III may be introduced directly into the cancer cells by, for example, the microinjection method while maintaining the GnT-III activity. Alternatively, the object of the present invention can be achieved by introducing a GnT-III gene into cancer cells with the use of, for example, a virus followed by the expression of GnT-III.

That is to say, the use of the drug of the present invention makes it possible to introduce GnT-III or a gene coding for GnT-III into cancer cells or the tissues therearound to thereby inhibit cancerous metastasis. When the cancer is located on the surface of a tissue, GnT-III or a gene coding for GnT-III may be injected directly into the affected part. Also when the cancer is located inside a tissue, GnT-III or a gene coding therefor may be injected directly into the affected part, or it is also possible to use a drug delivery system. The drug delivery system (DDS) may be selected from among commonly employed ones which are specific to cancer cells. For example, those with the use of a cancer cell receptor, a cancer-specific antibody, etc., may be used therefor. Also, it is a highly efficacious method for inhibiting cancerous metastasis to apply the drug of the present invention to the tissues around the affected part at the enucleation of a cancer tissue.

In the application of the drug of the present invention comprising GnT-III or a gene thereof to cancer cells or the tissues therearound, it is a matter of course to endeavor to utilize its efficacy to the full.

The cancerous metastasis inhibitor of the present invention may be processed into a preparation in the same manner as those employed for the production of usual drugs for gene therapy or preparations containing proteins, so long as it contains GnT-III or a gene thereof in an amount falling within a pharmaceutically acceptable range. The preparation may further contain carriers, fillers, stabilizers, thickening agents, etc.

The dose of GnT-III or a gene thereof to be used as the cancerous metastatis inhibitor of the present invention may be appropriately regulated by considering the conditions (age, body weight, etc.) of the patient and the stage of the affected part.

GnT-III or a gene thereof contained in the cancerous metastasis inhibitor of the present invention is a substance occurring in vivo and thus having no toxicity.

The enzymological properties of GnT-III to be used in the present invention have been already clarified in detail. This enzyme can be prepared from, for example, rat kidney in accordance with the method shown in Table 1.

TABLE 1

| Step | Specific activity (nmol/mg/hr) |
|---|---|
| 1. homogenate | 2.16 |
| 2. Triton extract | 8.94 |
| 3. QAE-Sepharose | 42.1 |
| 4. Hydroxyapatite | 74.6 |
| 5. $Cu^{2+}$-chelating Sepharose | 248 |
| 6. Con A Sepharose | 578 |
| 7. $Cu^{2+}$-chelating Sepharose | 820 |
| 8. UDP-hexanolamine agarose | 7,230 |
| 9. Gn, Gn-bi-Asn Sepharose | 331,000 |

In Table 1, Gn, Gn-bi-Asn represents GlcNAcβ1-2Manα1 -6 (GlcNAcβ1-2Manα1-3)Manβ1-4GlcNAcβ1-4GlcNAc-Asn. The GnT-III activities are measured in accordance with the method described in Biochimica et Biophysica Acta, 1035 (3), 313–318 (1990) by using 80 μM of a fluorescent substrate. The specific activities of the enzyme are expressed in GlcNAc (mol) transferred/protein (mg)/time (hr) by using pyridyl(-2-) aminated GlcNAc as a standard. The protein is assayed by using a BCA kit (mfd. by Pierce) with the use of serum albumin as a standard.

The gene of GnT-III may be obtained from, for example, a human fetal liver cDNA library in accordance with the method of Ihara et al. [Journal of Biochemistry, 113, 692–698 (1993)]. Also, a gene obtained from, for example, a rat liver cDNA library in accordance with the method of Nishikawa et al. [Journal of Biological Chemistry, 267, 18199–18204 (1992)] can be appropriately used as an experimental material in studying the inhibition of cancerous metastasis.

Further, rat GnT-III may be prepared by, for example, the method described in Japanese Patent Laid-Open No. 38767/1994 with the use of FERM BP-4352.

Furthermore, human GnT-III may be prepared by, for example, the method described in U.S. patent appln. Ser. No. 08/107,173.

The DNA sequence of a gene coding for rat GnT-III and the amino acid sequence thereof are represented by SEQ ID No. 3 and 5, respectively, of the Sequence Listing. The DNA sequence of a gene coding for human GnT-III and the amino acid sequence thereof are represented by SEQ ID No. 2 and 4, respectively, of the Sequence Listing. By using such a gene as a probe, a gene which codes for a protein having GnT-III activity and is hybridizable with the above-mentioned gene can be prepared. Alternatively, the gene represented by SEQ ID No. 3 or 2 of the Sequence Listing may be subjected to, for example, genetic engineering replacement, mutation or cleavage to thereby prepare a gene which codes for a protein having GnT-III activity and is hybridizable with the above-mentioned gene.

These genes and the expression products thereof are also usable as a drug of the present invention.

When GnT-III of the drug of the present invention is to be introduced into cells by using a gene per se, the GnT-III gene can be easily introduced into the cells by using a recombinant vector having the GnT-III gene and a regulator gene relating thereto. Thus, use can be made of not only a promoter of GnT-III per se but also other effective promoters such as an SV40 promoter, an LTR promoter from a retro virus, a heat shock promoter, a metallothionein promoter and an actin promoter.

In the introduction of the GnT-III gene, a cancer tissue or an uncancerized tissue can be efficiently infected with a vector containing this gene by using a virus vector. As such a vector, use can be made of a virus which has been known as transporting the target DNA and having a high infection efficiency, such as a retro virus, vaccinia virus, adenovirus or a nonproliferative recombinant virus. Among these viruses, a nonproliferative recombinant virus, which would not proliferate after the introduction into the target cells and thus should be renewed at intervals, of two weeks to two months, has a merit that its amount can be controlled each time. Also, liposomes, i.e., artificial lipid capsules may be used therefor.

A vector which is desirable as the drug of the present invention may be constructed by the following method. The cDNA of human GnT-III is introduced into the EcoRI site of a pCAGGS vector (FIG. 8) provided by Dr. Kenichi Yamamura, Kumamoto University, to thereby form an expression vector of GnT-III regulated by an actin promoter.

Regarding cancerous metastasis, the possibility of metastasis can be evaluated by, for example, measuring the activity of the treated cells to form metastatic nodes in mouse lungs. More specifically, a DNA obtained by linearizing the above-mentioned expression vector of GnT-III with SalI is mixed with another DNA obtained by linearizing pSV2-neo [Japanese Cancer Research Bank, a vector having a neomycin (G418)-tolerant gene] with BamHI (mfd. by Takara Shuzo Co., Ltd.) at a ratio of 10:1 and then introduced into mouse melanoma cells by the electroporation method. After incubating in a medium containing the antibiotic G418, tolerant cell lines are screened therefrom. Several cell lines expressing the GnT-III activity thus obtained are selected and incubated to give the semiconfluent state. Then cells are peeled off the plate and collected to thereby prepare cell suspensions. Each cell suspension is then intravenously injected into the tails of a group of seven C57BL/6 mice aged 5 weeks. After 21 days, the lungs are taken out and melanoma colonies are counted to thereby evaluate the ability of the cancer cells to metastasize. Alternatively, the ability of the cancer cells to metastasize can be evaluated by examining the mobility of the cells in vitro by, for example, the Matrigel assay method with the use of a Matrigel invasion chamber [Cancer Research, 52, 3610 (1992)].

Thus the present inventors have compared the ability of the mouse melanoma cells having the GnT-III gene introduced therein to metastasize with that of cells having no GnT-III gene. As a result, they have found that cells having the GnT-III gene introduced thereinto clearly show a decrease in the metastatic potential thus completing the present invention.

The drug of the present invention is useful in the field of cancer therapy.

To further illustrate the present invention in greater detail, but not by way of limitation, the following Examples are presented.

EXAMPLE 1

(1) Screening of cDNA Library

SV3 was prepared from *Escherichia coli* XL1-Blue SV3 (FERM BP-4325) transformed by a plasmid SV3 and the plasmid was digested with HindIII to give a DNA fragment of approximately 1.4 kb. This DNA fragment was radiolabeled with [$\alpha$-$^{32}$P] dCTP (3000 Ci/mmol, Amersham) by using a Multiprime DNA Labeling System (Amersham) to thereby give a probe. By using the obtained probe, a human cDNA library [Human Fetal Liver <λgt10>, Clonetech] was screened for the target clone by plaque hybridization. As a result, two positive clones were obtained from $3 \times 10^6$ plaques. From these clones, DNAs were extracted and digested with EcoRI. The digestion products thus obtained were subcloned into Bluescript IISK$^+$ and the DNAs thus subcloned (approximately 1.3 kb and approximately 1.5 kb) were respectively named H2 and H3, while the plasmids were respectively named pBluescript II (H2) and pBluescript II (H3). FIG. 2 shows the restriction maps of these DNAs and a relationship between them.

(2) Cloning of Upstream Region Containing Initiator Codon

H2 and H3 were radiolabeled in the same manner as described above to give probes. By using these probes, screening of a human cDNA library was carried out in the same manner as described above to obtain four positive clones from $7 \times 10^5$ plaques. The EcoRI-digestion products thereof were subcloned into Bluescript IISK$^+$. The base sequences of the DNAs thus subcloned were identified and two DNAS containing an initiator codon (approximately 1.6 kb and approximately 1.5 kb) were named respectively H15 and H20, while the plasmids corresponding thereto were named respectively pBluescript II (H15) and pBluescript II (H20). FIG. 2 shows the restriction maps of these DNAs and a relationship between them and H2 and H3.

EXAMPLE 2

(1) Construction of Expression Plasmid

The pBluescript II (H20) prepared in Example 1 was digested with EcoRI to excise H20, which was integrated into the EcoRI site of an expression vector pSVK3 (Pharmacia) for eucaryotic cells to thereby give pSVK (H20). Separately, the pBluescript II (H3) prepared in the above Example 1 was digested with NotI and XhoI to obtain an NotI-XhoI fragment (approximately 0.9 kb) containing the downstream region of the human GnT-III gene. Next, an expression plasmid EX20F for eucaryotic cells was constructed by digesting pSVK(H20) with NotI and XhoI, excising the NotI-XhoI fragment away, and integrating the NotI-XhoI fragment (approximately 0.9 kb) of pBluescript II (H3) in its place (see FIG. 3).

The base sequence of the DNA fragment integrated into EX20F was determined by the dideoxy method. A part of this base sequence is represented by SEQ ID NO. 1 in the sequence listing. As the result of screening for an ORF, an ORF was found in the bases Nos. 169 to 1761. FIG. 1 shows a restriction map of this ORF region. SEQ ID NO. 2 in the sequence listing shows the nucleic acid sequence and SEQ ID NO. 4 shows the deduced amino acid sequence of the ORF region.

(2) Transformation and Expression of Human GnT-III Gene

The COS-1 cells to be used for expressing human GnT-III were incubated in Dulbecco's modified Eagle medium containing 10% of FCS in the presence of 5% of $CO_2$ at 37° C. under moist conditions.

Subsequently, the EX20F prepared in the above Example 2-(1) was introduced into the COS-1 cells by electroporation with the use of a Gene Pulser (Bio-Rad). More specifically, approximately $5\times10^6$ cells and a recombinant plasmid or a control vector were suspended in 0.8 ml of 20 mM Hepes buffer (pH 7.05) containing 137 mM of NaCl, 5 mM of KCl, 0.7 mM of $Na_2HPO_4$ and 6 mM of dextrose, and treated at a voltage of 250 V/0.4 cm and at a capacitance of 960 µF.

After the completion of the transformation, incubation was carried out for 2 days and then the cells were harvested and sonicated in PBS to determine the GnT-III activity in the sonicated cell suspension. It was found that the cells which had not been treated with the plasmid and those which had been treated with the control plasmid pSVK3 had no GnT-III activity, whereas the cells transformed by the plasmid EX20F had a GnT-III activity, suggesting that the human GnT-III gene had been expressed therein.

Thus it has been proved that a gene coding for human GnT-III exists on the DNA fragment which has been integrated into EX20F and a part of the base sequence of which is represented by SEQ ID NO. 1 in the Sequence Listing hereinafter.

(3) Determination of GnT-III Activity

The GnT-III activity was determined in accordance with the description given in Biochimica et Biophysica Acta, 1035, 313–318 (1990). More precisely, by using 80 µM of pyridylamino (PA) Gn, Gn-bi [GlcNAc β1-2Man α1-6 (GlcNAc β1-2Man α1-3)Man β1-4 GlcNAc β1-4 GlcNAc-PA] as a receptor, UDP-GlcNAc serving as a sugar donor was added in such a manner as to give a final concentration of 80 µM to a 125 mM solution of 2-(N-morpholino) ethanesulfonic acid buffer (MES buffer, pH 6.25) containing 10 mM of $MnCl_2$, 200 mM of GlcNAc and 0.5% (v/v) of Triton X-100. After reacting the mixture at 37° C. for 1 hour, the GnT-III activity was determined by analyzing by HPLC.

EXAMPLE 3

[Construction of Expression Vector and Introduction Thereof into Cells]

The 5' noncoding region (42 bp) of a cDNA clone C4 containing the full length of a region coding for rat GnT-III [Journal of Biological Chemistry, 267, 18199–18204 (1992)] was eliminated by digesting with exonuclease III (ExoIII, mfd. by Takara Shuzo Co., Ltd.) and mung bean nuclease (mfd. by Takara Shuzo Co., Ltd.).

Figure 8:
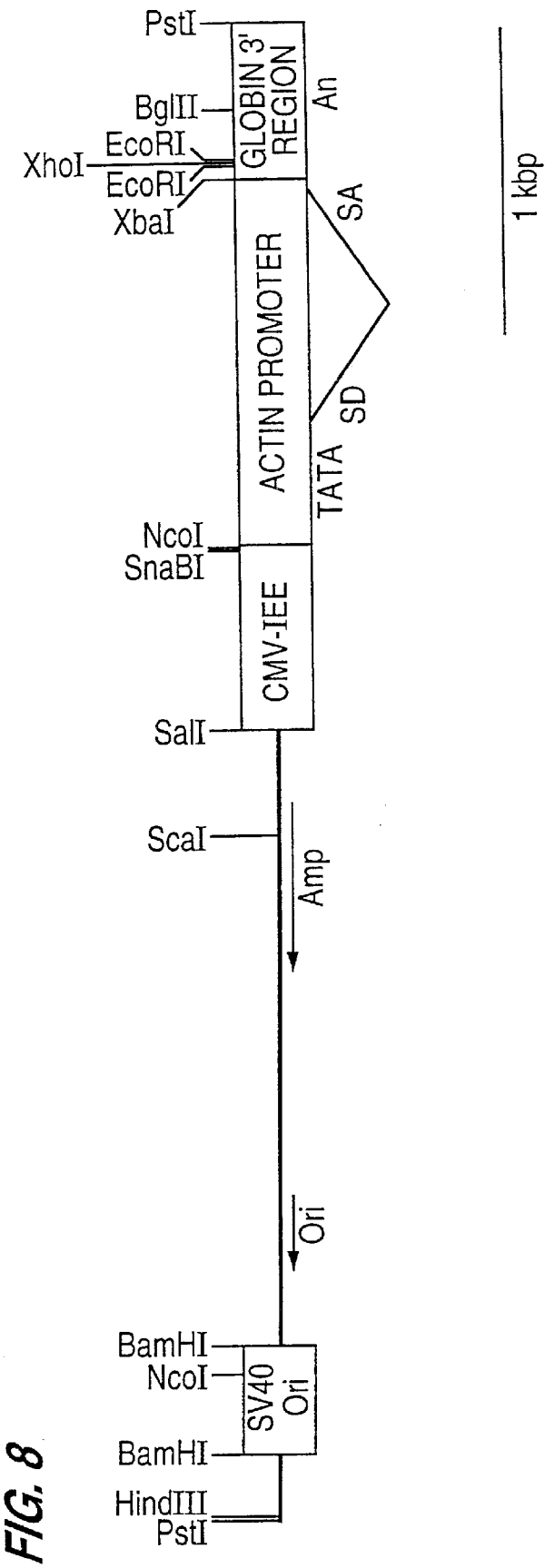
FIG. 8 shows the restriction map of a pCAGGS vector.

The C4 fragment thus shortened was digested with EcoRI (mfd. by Takara Shuzo Co., Ltd.), blunted by the Klenow treatment and then subcloned into the SmaI site of a pSVK3 vector (mfd. by Pharmacia). Then the SacI fragment was excised therefrom and blunted with T4DNA polymerase (mfd. by Takara Shuzo Co., Ltd.). Then it was subcloned into the EcoRI site of a pCAGGS vector (provided by Dr. Kenichi Yamamura, Kumamoto University) which had been similarly blunted by the Klenow treatment. FIG. 8 shows the restriction map of the pCAGGS vector.

Figure 4:
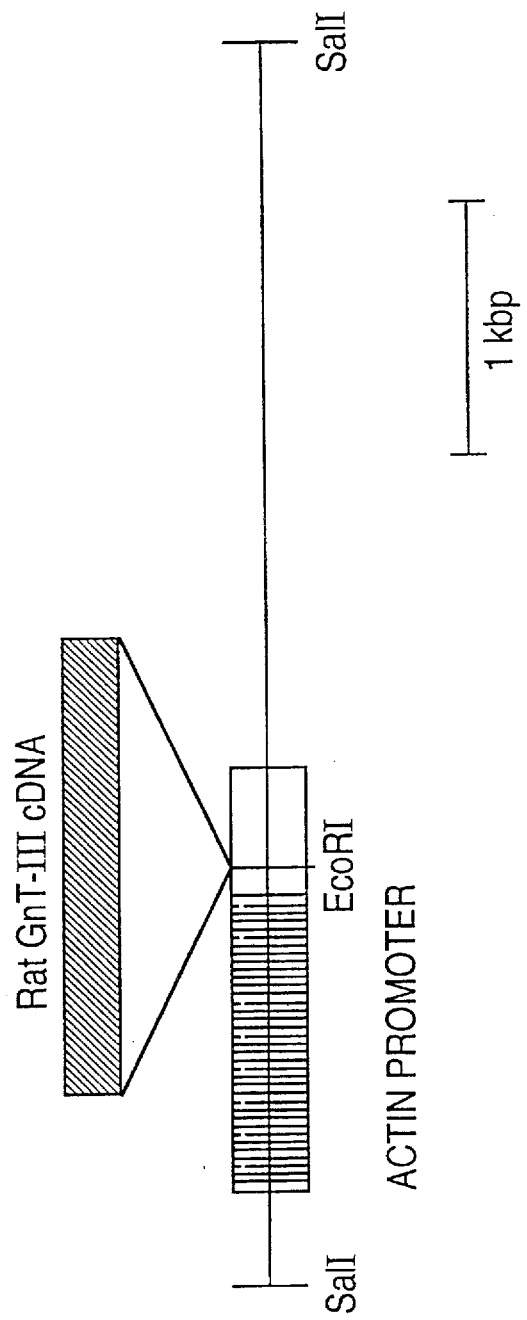
FIG. 4 is a model view of GnT-III expression plasmid Act-3.

The expression plasmid thus constructed was named GnT-III expression plasmid Act-3. In this GnT-III expression plasmid Act-3, the expression of GnT-III is regulated by an actin promoter. FIG. 4 is a model view of the GnT-III expression plasmid Act-3. In FIG. 4, the broad and solid line (black) at the upper section shows the cDNA of rat GnT-III, while the lower section shows the pCAGGS vector (FIG. 8). The hatched part in the lower section indicates the actin promoter.

This GnT-III expression plasmid Act-3 and a pSV2-neo vector [Japanese Cancer Research Bank, a vector having a neomycin (G418)-tolerant gene] were linearized by digesting respectively with SalI (mfd. by Takara Shuzo Co., Ltd.) and BamHI (mfd. by Takara Shuzo Co., Ltd.). Then 20 µg of the GnT-III expression plasmid Act-3 was mixed with 2 µg of the pSV2-neo vector and introduced into mouse melanoma B16-F1 cells by the electroporation method with the use of a Gene Pulser (mfd. by Bio Rad: voltage: 250 V/0.4 cm, electrostatic capacity: 960 µF). The cells having the gene introduced thereinto were selected on a medium containing G418 (1 mg/ml, mfd. by GIBCO BRL) and tolerant cell lines were cloned by dilution. As a result, nine cell lines having the GnT-III activity and three cell lines showing no GnT-III activity were obtained. From the cell lines having the GnT-III activity, three cell lines were arbitrarily selected and named F1-GnT-III-1, F1-GnT-III-2 and F1-GnT-III 3, while two cell lines were selected from among those having no GnT-III activity and named F1-neo-1 and F1-neo-2.

[Enzyme Activities of GnT-III and GnT-V of Cells]

Table 2 presented herein shows the GnT-III, GnT-V and galactosyl-transferase (Gal-T) activities in the cells, the number of copies of the GnT-III gene introduced thereinto, the proliferation rates and the abilities to form colonies.

In Table 2, "a" indicates the activities of the enzymes GnT-III, GnT-V and Gal-T determined by using a sugar chain fluorolabeled with 2-aminopyridine as a substrate in accordance respectively with the methods described in Analytical Biochemistry, 170, 349–354 (1988), Methods in Enzymology, 179, 397–408 (1985) and Journal of Biological Chemistry, 265, 6009–6018 (1990). In Table 2, "b" indicates the numbers of copies of the introduced GnT-III gene measured by the Southern blot technique, while "c" indicates the proliferation rates and the abilities to form colonies of the cells which had been determined by repeating the test thrice. Also, "d" and "e" give the results of statistical treatment according to Student's t test, showing possibilities [d]p<0.001 and [e]p<0.05 each for B16-F1. The expression "p<0.001" means being identical with B16-F1 at a possibility lower than 0.001.

TABLE 2

| | Enzyme activity (pmol/h/mg)[a] | | | Number of copies of GnT- | | Ability to form |
| --- | --- | --- | --- | --- | --- | --- |
| Cell | GnT-III | GnT-V | Gal-T | III gene introduced[b] | Proliferation rate[c] | colonies[c] |
| F1 | not detected | 758 ± 35 | 2,150 ± 188 | not detected | 100 | 116 ± 7 |
| F1-neo-1 | not detected | 743 ± 222 | 1,760 ± 189 | not detected | 112 ± 10 | 69 ± 8[e] |
| F1-neo-2 | not detected | 861 ± 74 | 1,410 ± 267 | not detected | 107 ± 11 | 82 ± 8 |
| F1-GnT-III-1 | 125,000 ± 2,000[d] | 1,080 ± 61 | 2,720 ± 632 | 1 | 80 ± 13 | 128 ± 7 |

TABLE 2-continued

| Cell | Enzyme activity (pmol/h/mg)[a] | | | Number of copies of GnT-III gene introduced[b] | Proliferation rate[c] | Ability to form colonies[c] |
|---|---|---|---|---|---|---|
| | GnT-III | GnT-V | Gal-T | | | |
| F1-GnT-III-2 | 164,000 ± 5,200[d] | 1,350 ± 112 | 2,840 ± 329 | 2 | 119 ± 13 | 10 ± 10 |
| F1-GnT-III-3 | 92,100 ± 3,070[d] | 1,280 ± 158 | 1,990 ± 293 | 2 | 86 ± 10 | 58 ± 7[e] |

As Table 2 shows, the GnT-III activity was elevated to 92,100 to 164,000 pmol/h/mg protein in the GnT-III positive cells. On the other hand, the GnT-V and Gal-T activities of the transformed cell lines were scarcely different from those of the parent cell line.

Figure 5:
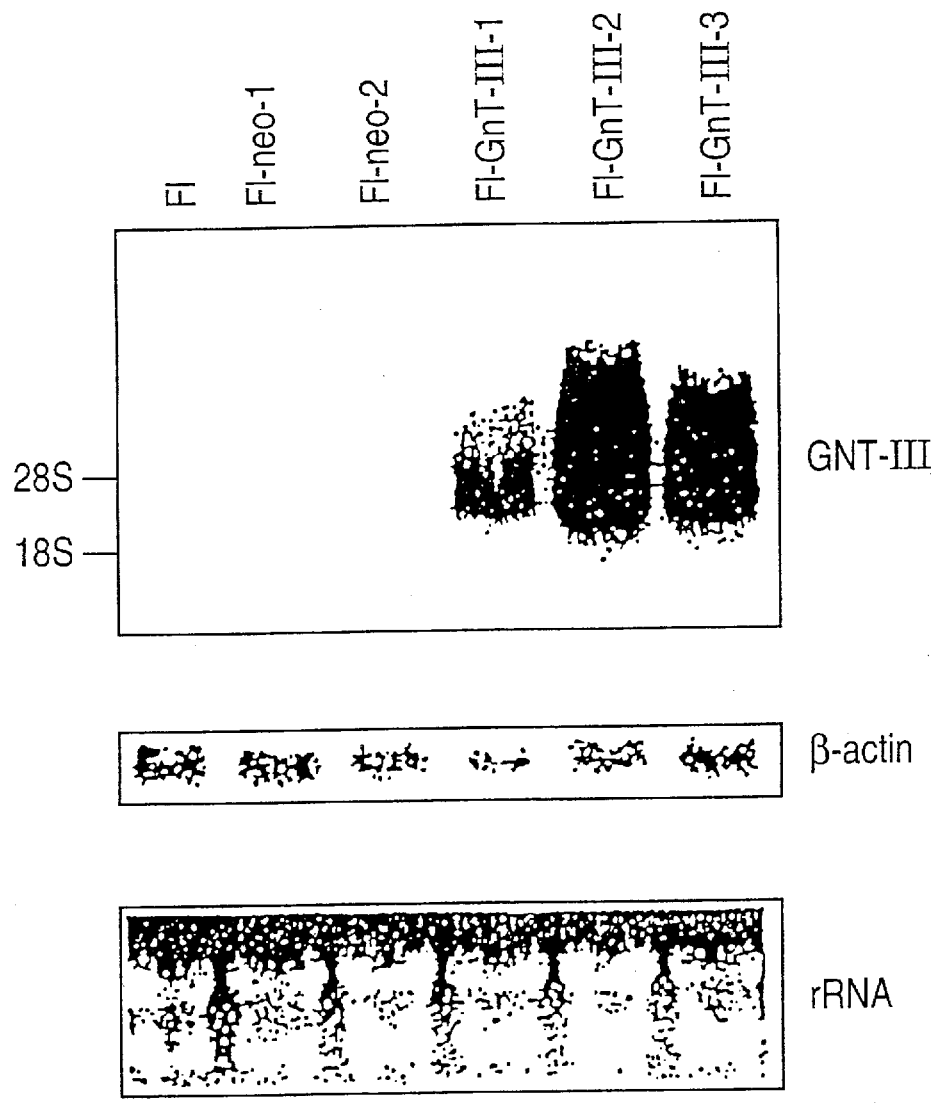
FIG. 5 shows the amount of a GnT-III transcript (mRNA) in B16-Fl cells.

The amount of the GnT-III transcript (mRNA) in the B16-Fl cells was determined. FIG. 5 shows the amount of the GnT-III transcript (mRNA) in the B16-Fl cells. The amounts of the GnT-III transcript (mRNA), β-actin and ribosomal RNA (rRNA) are shown respectively in the upper, middle and lower sections. Fl-GnT-III-2 shows the maximum level of the mRNA of GnT-III, while Fl-GnT-III-1 shows the minimum level thereof.

[Evaluation of Cancerous Metastasis]

Figure 6:
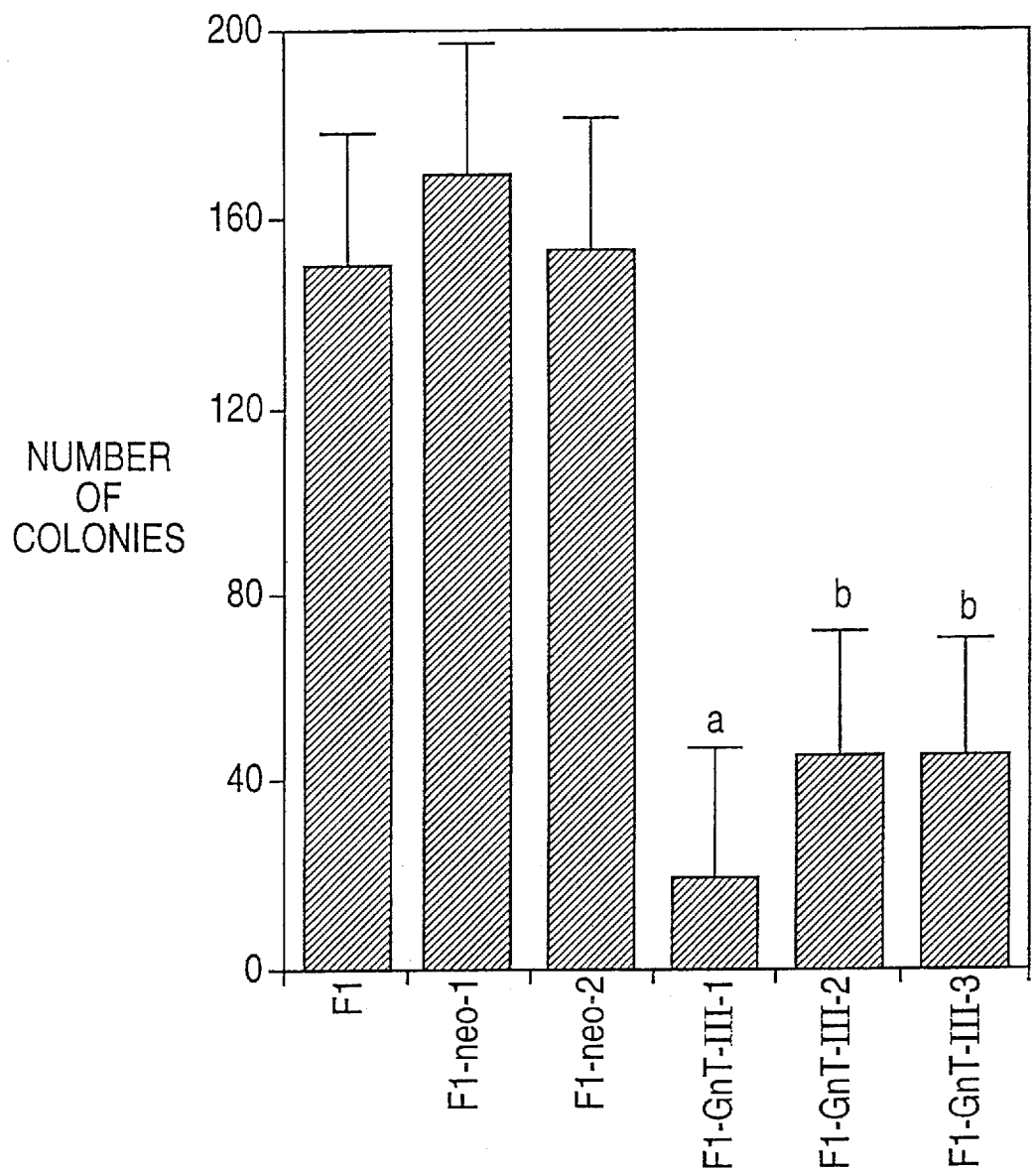
FIG. 6 shows the results of an evaluation of the metastatic potential in vivo.

The abilities of the cells to metastasize in vivo were evaluated in the following manner. The B16-Fl cells and the transformed cells each at the logarithmic growth phase were peeled off the plates by using phosphate-buffered saline (PBS) and the cells were counted. Vital cells were suspended in Hank's buffer and intravenously injected into the tails of a group of seven C57BL/6 mice aged 5 weeks ($3\times10^5$ cells/0.5 ml/animal). After 21 days, the lungs were taken out of the mice and fixed with Bouin's solution and then colonies were counted. FIG. 6 shows the data of the number of colonies. Namely, FIG. 6 shows the results of an evaluation of the ability to metastasize in vivo wherein the ordinate represents the number of colonies and the abscissa represents the cells subjected to the experiment. The bar stands for the average standard error of the data of the experiment repeated thrice. The data were statistically treated in accordance with Student's t test. $^a p<0.01$, $^b p<0.05$ vs. B16-Fl.

When the transformed cells negative to GnT-III were administered, the number of the metastasized colonies were almost the same as that of the parent strain, i.e., the B16-Fl cells. In contrast, the administration of the GnT-III positive cells clearly caused a decrease in the number of the metastasized colonies.

Figure 7:
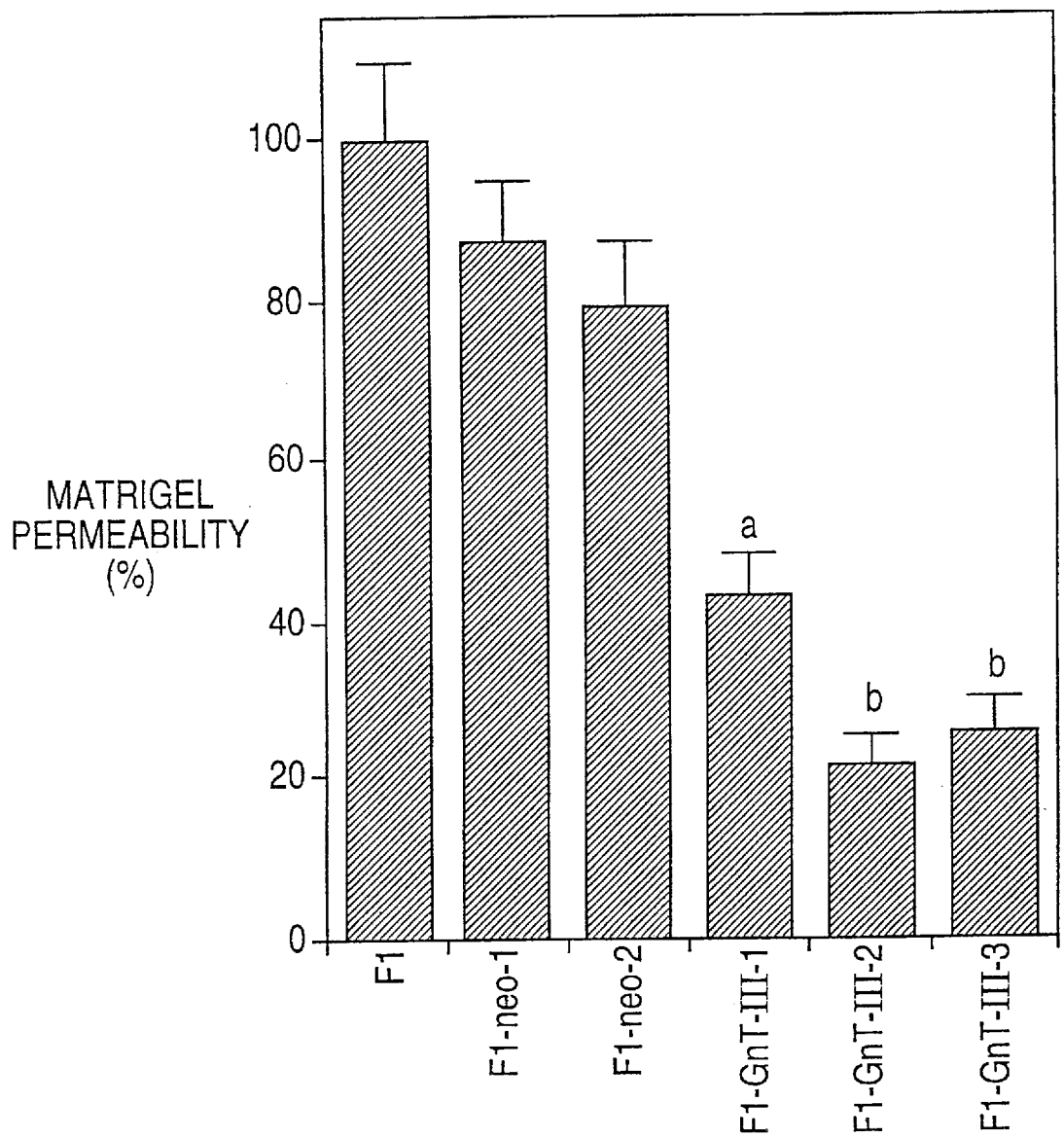
FIG. 7 shows the results of an evaluation of the ability to infiltrate in vitro.

The abilities of the cells to infiltrate in vitro were evaluated by the Matrigel assay method with the use of a Matrigel invasion chamber [BIOCOAT MATRIGEL, mfd. by Becton Dickinson]. FIG. 7 shows the results of an evaluation of the ability to infiltrate in vitro wherein the ordinate represents the number of cells permeating through the Matrigel expressed by taking the data of the B16-Fl cells (i.e., a control) as 100% (average±S.D.) and the abscissa represents the cells subjected to the experiment. The data were statistically treated in accordance with Student's t test. $^a p<0.01$, $^b p<0.05$ vs. B16-Fl.

It has thus been shown that the abilities to infiltrate are also suppressed in the GnT-III positive cells.

CONCLUSION

According to the present invention, a gene for human GnT-III having an important role in vivo and an industrial process for producing this enzyme are provided. The gene and enzyme are useful in the fields of, for example, biochemistry and diagnosis.

Also, the present invention provides a cancerous metastasis inhibitor comprising GnT-III or a gene thereof, by which the GnT-III activity of cancer cells or the tissues therearound is increased, as the active ingredient. This cancerous metastasis inhibitor is useful in the field of cancer therapy.

Although the present invention has been described in some detail by way of illustration and example for purposes of clarity and understanding, certain obvious modifications can be practiced within the scope of the appended claims.

What is claimed is:

1. An isolated or purified polypeptide having an amino acid sequence represented by SEQ ID NO:4.

2. A cancerous metastasis inhibitor comprising the isolated or purified polypeptide of claim 1, and a carrier therefor.

3. A method for inhibiting cancerous metastasis in a mammal comprising administering to the mammal a cancerous metastasis inhibiting amount of the isolated or purified polypeptide of claim 1 in an amount effective to inhibit said cancerous metastasis.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2247 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:1:

```
CCGGCTGCGA   TGCCGGGCGC   CCGCCGCAGC   CGCTGCCGCC   GGAGCCCGGG   ATGGGGCGAG         60
```

-continued

| | | | | | | |
|---|---|---|---|---|---|---|
| AGGCTGCGGC | GGACGCCAGC | ATCTCCCCGC | CGGGGACCCC | GGGGGCCGCG | GAGCCGCCGC | 120 |
| CGCCGCTGCT | GCCGCCGTTG | CTGAGACCCA | GCGGGCGATG | GGATGAAGAT | GAGACGCTAC | 180 |
| AAGCTCTTTC | TCATGTTCTG | TATGGCCGGC | CTGTGCCTCA | TCTCCTTCCT | GCACTTCTTC | 240 |
| AAGACCCTGT | CCTATGTCAC | CTTCCCCCGA | GAACTGGCCT | CCCTCAGCCC | TAACCTGGTG | 300 |
| TCCAGCTTTT | TCTGGAACAA | TGCCCCGGTC | ACGCCCAGG | CCAGCCCCGA | GCCAGGAGGC | 360 |
| CCTGACCTGC | TGCGTACCCC | ACTCTACTCC | CACTCGCCCC | TGCTGCAGCC | GCTGCCGCCC | 420 |
| AGCAAGGCGG | CCGAGGAGCT | CCACCGGGTG | GACTTGGTGC | TGCCCGAGGA | CACCACCGAG | 480 |
| TATTTCGTGC | GCACCAAGGC | CGGCGGCGTC | TGCTTCAAAC | CCGGCACCAA | GATGCTGGAG | 540 |
| AGGCCGCCCC | CGGGACGGCC | GGAGGAGAAG | CCTGAGGGGG | CCAACGGCTC | CTCGGCCCGG | 600 |
| CGGCCACCCC | GGTACCTCCT | GAGCGCCCGG | GAGCGCACGG | GGGGCCGAGG | CGCCCGGCGC | 660 |
| AAGTGGGTGG | AGTGCGTGTG | CCTGCCCGGC | TGGCACGGAC | CCAGCTGCGG | CGTGCCCACT | 720 |
| GTGGTGCAGT | ACTCCAACCT | GCCCACCAAG | GAGCGGCTGG | TGCCCAGGGA | GGTGCCGCGC | 780 |
| CGCGTCATCA | ACGCCATCAA | CGTCAACCAC | GAGTTCGACC | TGCTGGACGT | GCGCTTCCAC | 840 |
| GAGCTGGGCG | ACGTGGTGGA | CGCCTTTGTG | GTGTGCGAGT | CCAACTTCAC | GGCTTATGGG | 900 |
| GAGCCGCGGC | CGCTCAAGTT | CCGGGAGATG | CTGACCAATG | GCACCTTCGA | GTACATCCGC | 960 |
| CACAAGGTGC | TCTATGTCTT | CCTGGACCAC | TTCCCGCCCG | GCGGCCGGCA | GGACGGCTGG | 1020 |
| ATCGCCGACG | ACTACCTGCG | CACCTTCCTC | ACCCAGGACG | GCGTCTCGCG | GCTGCGCAAC | 1080 |
| CTGCGGCCCG | ACGACGTCTT | CATCATTGAC | GATGCGGACG | AGATCCCGGC | CCGTGACGGC | 1140 |
| GTCCTTTTCC | TCAAGCTCTA | CGATGGCTGG | ACCGAGCCCT | TCGCCTTCCA | CATGCGCACG | 1200 |
| TCGCTCTACG | GCTTCTTCTG | GAAGCAGCCG | GGCACCCTGG | AGGTGGTGTC | AGGCTGCACG | 1260 |
| GTGGACATGC | TGCAGGCAGT | GTATGGGCTG | GACGGCATCC | GCCTGCGCCG | CCGCCAGTAC | 1320 |
| TACACCATGC | CCAACTTCAG | ACAGTATGAG | AACCGCACCG | CCACATCCT | GGTGCAGTGG | 1380 |
| TCGCTGGGCA | GCCCCCTGCA | CTTCGCCGGC | TGGCACTGCT | CCTGGTGCTT | CACGCCCGAG | 1440 |
| GGCATCTACT | TCAAGCTCGT | GTCCGCCCAG | AATGGCGACT | TCCCACGCTG | GGGTGACTAC | 1500 |
| GAGGACAAGC | GGGACCTGAA | CTACATCCGC | GGCCTGATCC | GCACCGGGGG | CTGGTTCGAC | 1560 |
| GGCACGCAGC | AGGAGTACCC | GCCTGCAGAC | CCCAGCGAGC | ACATGTATGC | GCCCAAGTAC | 1620 |
| CTGCTGAAGA | ACTACGACCG | GTTCCACTAC | CTGCTGGACA | ACCCCTACCA | GGAGCCCAGG | 1680 |
| AGCACGGCGG | CGGGCGGGTG | GCGCCACAGG | GGTCCCGAGG | GAAGGCCGCC | CGCCCGGGGC | 1740 |
| AAACTGGACG | AGGCGGAAGT | CTAGAGCTGC | ATGATCTGAT | AGGGTTTGTG | ACAGGGCGGG | 1800 |
| GGTGGCGGCG | GCCCCTAGCG | CTATCTCCCT | GCCTCCTGCC | GGCTCCTTGG | TTCTTGAGGG | 1860 |
| GACCAGGAGT | GGGTGGGGAG | TGGGGGTGGG | GCTAGGGTTT | CCCTACTGAA | GCCCTTGTGA | 1920 |
| TCAAGGGTCA | GGCCTTTGAG | CTCAGAAAAT | ATCCCTCCTG | TTGGGAGAGG | GCGCAGGCCG | 1980 |
| TGACGTCTGG | GTGGCCCTTA | TGACTGCCAA | GACTGCTGTG | CCAGGAGGT | GCCACTGGAG | 2040 |
| TGTGCGTGGT | GGTCCCTGGG | TAGCGGGGGA | GGGTAGGCAG | GATTGGGGAA | GAGAGCCTGC | 2100 |
| AGGATCTCAC | CAGGCAGCCT | CTGGGGGGTG | GCCAGGCCGG | AAAAAGCCCA | CCATTTGGCA | 2160 |
| TCCCTGGGCC | TTGGGCTCCG | TGTGGGAGAC | CGGCCTGCCA | GGAGGACCCA | GGGCTCTGTA | 2220 |
| AGTAGATGCA | TTTGGGTCCA | GGAGGAA | | | | 2247 |

( 2 ) INFORMATION FOR SEQ ID NO:2:

( i ) SEQUENCE CHARACTERISTICS:
        ( A ) LENGTH: 1593 base pairs
        ( B ) TYPE: nucleic acid -continued ( C ) STRANDEDNESS: double
( D ) TOPOLOGY: linear ( i i ) MOLECULE TYPE: cDNA to mRNA ( x i ) SEQUENCE DESCRIPTION: SEQ ID NO:2:

```
ATG AGA CGC TAC AAG CTC TTT CTC ATG TTC TGT ATG GCC GGC CTG       45
Met Arg Arg Tyr Lys Leu Phe Leu Met Phe Cys Met Ala Gly Leu
 1               5                  10                  15

TGC CTC ATC TCC TTC CTG CAC TTC TTC AAG ACC CTG TCC TAT GTC       90
Cys Leu Ile Ser Phe Leu His Phe Phe Lys Thr Leu Ser Tyr Val
                20                  25                  30

ACC TTC CCC CGA GAA CTG GCC TCC CTC AGC CCT AAC CTG GTG TCC      135
Thr Phe Pro Arg Glu Leu Ala Ser Leu Ser Pro Asn Leu Val Ser
                35                  40                  45

AGC TTT TTC TGG AAC AAT GCC CCG GTC ACG CCC CAG GCC AGC CCC      180
Ser Phe Phe Trp Asn Asn Ala Pro Val Thr Pro Gln Ala Ser Pro
                50                  55                  60

GAG CCA GGA GGC CCT GAC CTG CTG CGT ACC CCA CTC TAC TCC CAC      225
Glu Pro Gly Gly Pro Asp Leu Leu Arg Thr Pro Leu Tyr Ser His
                65                  70                  75

TCG CCC CTG CTG CAG CCG CTG CCG CCC AGC AAG GCG GCC GAG GAG      270
Ser Pro Leu Leu Gln Pro Leu Pro Pro Ser Lys Ala Ala Glu Glu
                80                  85                  90

CTC CAC CGG GTG GAC TTG GTG CTG CCC GAG GAC ACC ACC GAG TAT      315
Leu His Arg Val Asp Leu Val Leu Pro Glu Asp Thr Thr Glu Tyr
                95                 100                 105

TTC GTG CGC ACC AAG GCC GGC GGC GTC TGC TTC AAA CCC GGC ACC      360
Phe Val Arg Thr Lys Ala Gly Gly Val Cys Phe Lys Pro Gly Thr
               110                 115                 120

AAG ATG CTG GAG AGG CCG CCC CCG GGA CGG CCG GAG GAG AAG CCT      405
Lys Met Leu Glu Arg Pro Pro Pro Gly Arg Pro Glu Glu Lys Pro
               125                 130                 135

GAG GGG GCC AAC GGC TCC TCG GCC CGG CGG CCA CCC CGG TAC CTC      450
Glu Gly Ala Asn Gly Ser Ser Ala Arg Arg Pro Pro Arg Tyr Leu
               140                 145                 150

CTG AGC GCC CGG GAG CGC ACG GGG GGC CGA GGC GCC CGG CGC AAG      495
Leu Ser Ala Arg Glu Arg Thr Gly Gly Arg Gly Ala Arg Arg Lys
               155                 160                 165

TGG GTG GAG TGC GTG TGC CTG CCC GGC TGG CAC GGA CCC AGC TGC      540
Trp Val Glu Cys Val Cys Leu Pro Gly Trp His Gly Pro Ser Cys
               170                 175                 180

GGC GTG CCC ACT GTG GTG CAG TAC TCC AAC CTG CCC ACC AAG GAG      585
Gly Val Pro Thr Val Val Gln Tyr Ser Asn Leu Pro Thr Lys Glu
               185                 190                 195

CGG CTG GTG CCC AGG GAG GTG CCG CGC CGC GTC ATC AAC GCC ATC      630
Arg Leu Val Pro Arg Glu Val Pro Arg Arg Val Ile Asn Ala Ile
               200                 205                 210

AAC GTC AAC CAC GAG TTC GAC CTG CTG GAC GTG CGC TTC CAC GAG      675
Asn Val Asn His Glu Phe Asp Leu Leu Asp Val Arg Phe His Glu
               215                 220                 225

CTG GGC GAC GTG GTG GAC GCC TTT GTG GTG TGC GAG TCC AAC TTC      720
Leu Gly Asp Val Val Asp Ala Phe Val Val Cys Glu Ser Asn Phe
               230                 235                 240

ACG GCT TAT GGG GAG CCG CGG CCG CTC AAG TTC CGG GAG ATG CTG      765
Thr Ala Tyr Gly Glu Pro Arg Pro Leu Lys Phe Arg Glu Met Leu
               245                 250                 255

ACC AAT GGC ACC TTC GAG TAC ATC CGC CAC AAG GTG CTC TAT GTC      810
Thr Asn Gly Thr Phe Glu Tyr Ile Arg His Lys Val Leu Tyr Val
               260                 265                 270

TTC CTG GAC CAC TTC CCG CCC GGC GGC CGG CAG GAC GGC TGG ATC      855
```

|     |     |     |     |     |     |     |     |     |     |     |     |     |     |     |
|-----|-----|-----|-----|-----|-----|-----|-----|-----|-----|-----|-----|-----|-----|-----|
| Phe | Leu | Asp | His | Phe<br>275 | Pro | Pro | Gly | Gly | Arg<br>280 | Gln | Asp | Gly | Trp | Ile<br>285 |

| GCC | GAC | GAC | TAC | CTG | CGC | ACC | TTC | CTC | ACC | CAG | GAC | GGC | GTC | TCG | 900 |
|-----|-----|-----|-----|-----|-----|-----|-----|-----|-----|-----|-----|-----|-----|-----|-----|
| Ala | Asp | Asp | Tyr | Leu<br>290 | Arg | Thr | Phe | Leu | Thr<br>295 | Gln | Asp | Gly | Val | Ser<br>300 | |

| CGG | CTG | CGC | AAC | CTG | CGG | CCC | GAC | GAC | GTC | TTC | ATC | ATT | GAC | GAT | 945 |
|-----|-----|-----|-----|-----|-----|-----|-----|-----|-----|-----|-----|-----|-----|-----|-----|
| Arg | Leu | Arg | Asn | Leu<br>305 | Arg | Pro | Asp | Asp | Val<br>310 | Phe | Ile | Ile | Asp | Asp<br>315 | |

| GCG | GAC | GAG | ATC | CCG | GCC | CGT | GAC | GGC | GTC | CTT | TTC | CTC | AAG | CTC | 990 |
|-----|-----|-----|-----|-----|-----|-----|-----|-----|-----|-----|-----|-----|-----|-----|-----|
| Ala | Asp | Glu | Ile | Pro<br>320 | Ala | Arg | Asp | Gly | Val<br>325 | Leu | Phe | Leu | Lys | Leu<br>330 | |

| TAC | GAT | GGC | TGG | ACC | GAG | CCC | TTC | GCC | TTC | CAC | ATG | CGC | ACG | TCG | 1035 |
|-----|-----|-----|-----|-----|-----|-----|-----|-----|-----|-----|-----|-----|-----|-----|------|
| Tyr | Asp | Gly | Trp | Thr<br>335 | Glu | Pro | Phe | Ala | Phe<br>340 | His | Met | Arg | Thr | Ser<br>345 | |

| CTC | TAC | GGC | TTC | TTC | TGG | AAG | CAG | CCG | GGC | ACC | CTG | GAG | GTG | GTG | 1080 |
|-----|-----|-----|-----|-----|-----|-----|-----|-----|-----|-----|-----|-----|-----|-----|------|
| Leu | Tyr | Gly | Phe | Phe<br>350 | Trp | Lys | Gln | Pro | Gly<br>355 | Thr | Leu | Glu | Val | Val<br>360 | |

| TCA | GGC | TGC | ACG | GTG | GAC | ATG | CTG | CAG | GCA | GTG | TAT | GGG | CTG | GAC | 1125 |
|-----|-----|-----|-----|-----|-----|-----|-----|-----|-----|-----|-----|-----|-----|-----|------|
| Ser | Gly | Cys | Thr | Val<br>365 | Asp | Met | Leu | Gln | Ala<br>370 | Val | Tyr | Gly | Leu | Asp<br>375 | |

| GGC | ATC | CGC | CTG | CGC | CGC | CGC | CAG | TAC | TAC | ACC | ATG | CCC | AAC | TTC | 1170 |
|-----|-----|-----|-----|-----|-----|-----|-----|-----|-----|-----|-----|-----|-----|-----|------|
| Gly | Ile | Arg | Leu | Arg<br>380 | Arg | Arg | Gln | Tyr | Tyr<br>385 | Thr | Met | Pro | Asn | Phe<br>390 | |

| AGA | CAG | TAT | GAG | AAC | CGC | ACC | GGC | CAC | ATC | CTG | GTG | CAG | TGG | TCG | 1215 |
|-----|-----|-----|-----|-----|-----|-----|-----|-----|-----|-----|-----|-----|-----|-----|------|
| Arg | Gln | Tyr | Glu | Asn<br>395 | Arg | Thr | Gly | His | Ile<br>400 | Leu | Val | Gln | Trp | Ser<br>405 | |

| CTG | GGC | AGC | CCC | CTG | CAC | TTC | GCC | GGC | TGG | CAC | TGC | TCC | TGG | TGC | 1260 |
|-----|-----|-----|-----|-----|-----|-----|-----|-----|-----|-----|-----|-----|-----|-----|------|
| Leu | Gly | Ser | Pro | Leu<br>410 | His | Phe | Ala | Gly | Trp<br>415 | His | Cys | Ser | Trp | Cys<br>420 | |

| TTC | ACG | CCC | GAG | GGC | ATC | TAC | TTC | AAG | CTC | GTG | TCC | GCC | CAG | AAT | 1305 |
|-----|-----|-----|-----|-----|-----|-----|-----|-----|-----|-----|-----|-----|-----|-----|------|
| Phe | Thr | Pro | Glu | Gly<br>425 | Ile | Tyr | Phe | Lys | Leu<br>430 | Val | Ser | Ala | Gln | Asn<br>435 | |

| GGC | GAC | TTC | CCA | CGC | TGG | GGT | GAC | TAC | GAG | GAC | AAG | CGG | GAC | CTG | 1350 |
|-----|-----|-----|-----|-----|-----|-----|-----|-----|-----|-----|-----|-----|-----|-----|------|
| Gly | Asp | Phe | Pro | Arg<br>440 | Trp | Gly | Asp | Tyr | Glu<br>445 | Asp | Lys | Arg | Asp | Leu<br>450 | |

| AAC | TAC | ATC | CGC | GGC | CTG | ATC | CGC | ACC | GGG | GGC | TGG | TTC | GAC | GGC | 1395 |
|-----|-----|-----|-----|-----|-----|-----|-----|-----|-----|-----|-----|-----|-----|-----|------|
| Asn | Tyr | Ile | Arg | Gly<br>455 | Leu | Ile | Arg | Thr | Gly<br>460 | Gly | Trp | Phe | Asp | Gly<br>465 | |

| ACG | CAG | CAG | GAG | TAC | CCG | CCT | GCA | GAC | CCC | AGC | GAG | CAC | ATG | TAT | 1440 |
|-----|-----|-----|-----|-----|-----|-----|-----|-----|-----|-----|-----|-----|-----|-----|------|
| Thr | Gln | Gln | Glu | Tyr<br>470 | Pro | Pro | Ala | Asp | Pro<br>475 | Ser | Glu | His | Met | Tyr<br>480 | |

| GCG | CCC | AAG | TAC | CTG | CTG | AAG | AAC | TAC | GAC | CGG | TTC | CAC | TAC | CTG | 1485 |
|-----|-----|-----|-----|-----|-----|-----|-----|-----|-----|-----|-----|-----|-----|-----|------|
| Ala | Pro | Lys | Tyr | Leu<br>485 | Leu | Lys | Asn | Tyr | Asp<br>490 | Arg | Phe | His | Tyr | Leu<br>495 | |

| CTG | GAC | AAC | CCC | TAC | CAG | GAG | CCC | AGG | AGC | ACG | GCG | GCG | GGC | GGG | 1530 |
|-----|-----|-----|-----|-----|-----|-----|-----|-----|-----|-----|-----|-----|-----|-----|------|
| Leu | Asp | Asn | Pro | Tyr<br>500 | Gln | Glu | Pro | Arg | Ser<br>505 | Thr | Ala | Ala | Gly | Gly<br>510 | |

| TGG | CGC | CAC | AGG | GGT | CCC | GAG | GGA | AGG | CCG | CCC | GCC | CGG | GGC | AAA | 1575 |
|-----|-----|-----|-----|-----|-----|-----|-----|-----|-----|-----|-----|-----|-----|-----|------|
| Trp | Arg | His | Arg | Gly<br>515 | Pro | Glu | Gly | Arg | Pro<br>520 | Pro | Ala | Arg | Gly | Lys<br>525 | |

| CTG | GAC | GAG | GCG | GAA | GTC | 1593 |
|-----|-----|-----|-----|-----|-----|------|
| Leu | Asp | Glu | Ala | Glu<br>530 | Val | |

( 2 ) INFORMATION FOR SEQ ID NO:3:

( i ) SEQUENCE CHARACTERISTICS:
        ( A ) LENGTH: 1608 base pairs
        ( B ) TYPE: nucleic acid
        ( C ) STRANDEDNESS: double
        ( D ) TOPOLOGY: linear (ii) MOLECULE TYPE: cDNA to genomic RNA (ix) SEQUENCE DESCRIPTION: SEQ ID NO: 3:

| ATG | AGA | CGC | TAC | AAG | CTT | TTT | CTC | ATG | TTC | TGT | ATG | GCC | GGC | CTG | 45 |
| Met | Arg | Arg | Tyr | Lys | Leu | Phe | Leu | Met | Phe | Cys | Met | Ala | Gly | Leu | |
| 1 | | | | 5 | | | | | 10 | | | | | 15 | |

| TGC | CTC | ATC | TCC | TTC | CTG | CAC | TTC | TTT | AAG | ACG | TTA | TCC | TAT | GTC | 90 |
| Cys | Leu | Ile | Ser | Phe | Leu | His | Phe | Phe | Lys | Thr | Leu | Ser | Tyr | Val | |
| | | | | 20 | | | | | 25 | | | | | 30 | |

| ACC | TTC | CCG | AGA | GAA | CTG | GCC | TCC | CTC | AGC | CCT | AAC | CTC | ATA | TCC | 135 |
| Thr | Phe | Pro | Arg | Glu | Leu | Ala | Ser | Leu | Ser | Pro | Asn | Leu | Ile | Ser | |
| | | | | 35 | | | | | 40 | | | | | 45 | |

| AGC | TTC | TTC | TGG | AAC | AAT | GCC | CCT | GTC | ACT | CCC | CAG | GCC | AGT | CCG | 180 |
| Ser | Phe | Phe | Trp | Asn | Asn | Ala | Pro | Val | Thr | Pro | Gln | Ala | Ser | Pro | |
| | | | | 50 | | | | | 55 | | | | | 60 | |

| GAG | CCC | GGT | GAC | CCC | GAC | TTG | TTA | CGG | ACT | CCA | CTC | TAC | TCC | CAC | 225 |
| Glu | Pro | Gly | Asp | Pro | Asp | Leu | Leu | Arg | Thr | Pro | Leu | Tyr | Ser | His | |
| | | | | 65 | | | | | 70 | | | | | 75 | |

| TCC | CCC | CTG | CTC | CAG | CCA | CTG | TCC | CCT | AGC | AAG | GCC | ACC | GAA | GAA | 270 |
| Ser | Pro | Leu | Leu | Gln | Pro | Leu | Ser | Pro | Ser | Lys | Ala | Thr | Glu | Glu | |
| | | | | 80 | | | | | 85 | | | | | 90 | |

| CTG | CAC | CGG | GTG | GAC | TTC | GTG | TTG | CCG | GAG | GAC | ACC | ACA | GAG | TAT | 315 |
| Leu | His | Arg | Val | Asp | Phe | Val | Leu | Pro | Glu | Asp | Thr | Thr | Glu | Tyr | |
| | | | | 95 | | | | | 100 | | | | | 105 | |

| TTT | GTG | CGC | ACC | AAA | GCT | GGC | GGT | GTG | TGC | TTC | AAA | CCA | GGT | ACC | 360 |
| Phe | Val | Arg | Thr | Lys | Ala | Gly | Gly | Val | Cys | Phe | Lys | Pro | Gly | Thr | |
| | | | | 110 | | | | | 115 | | | | | 120 | |

| AGG | ATG | CTG | GAG | AAA | CCT | TCT | CCA | GGG | CGG | ACA | GAG | GAG | AAG | ACC | 405 |
| Arg | Met | Leu | Glu | Lys | Pro | Ser | Pro | Gly | Arg | Thr | Glu | Glu | Lys | Thr | |
| | | | | 125 | | | | | 130 | | | | | 135 | |

| AAG | GTG | GCT | GAG | GGG | TCC | TCG | GTC | CGG | GGT | CCT | GCT | CGG | AGG | CCT | 450 |
| Lys | Val | Ala | Glu | Gly | Ser | Ser | Val | Arg | Gly | Pro | Ala | Arg | Arg | Pro | |
| | | | | 140 | | | | | 145 | | | | | 150 | |

| ATG | CGG | CAT | GTG | TTG | AGT | GCA | CGG | GAG | CGC | CTG | GGA | GGC | CGG | GGC | 495 |
| Met | Arg | His | Val | Leu | Ser | Ala | Arg | Glu | Arg | Leu | Gly | Gly | Arg | Gly | |
| | | | | 155 | | | | | 160 | | | | | 165 | |

| ACT | AGG | CGC | AAG | TGG | GTT | GAG | TGT | GTG | TGC | CTG | CCA | GGC | TGG | CAC | 540 |
| Thr | Arg | Arg | Lys | Trp | Val | Glu | Cys | Val | Cys | Leu | Pro | Gly | Trp | His | |
| | | | | 170 | | | | | 175 | | | | | 180 | |

| GGG | CCC | AGC | TGC | GGG | GTG | CCC | ACT | GTG | GTC | CAG | TAT | TCC | AAC | CTG | 585 |
| Gly | Pro | Ser | Cys | Gly | Val | Pro | Thr | Val | Val | Gln | Tyr | Ser | Asn | Leu | |
| | | | | 185 | | | | | 190 | | | | | 195 | |

| CCC | ACC | AAG | GAG | CGC | CTG | GTA | CCC | AGG | GAG | GTG | CCG | AGG | CGG | GTT | 630 |
| Pro | Thr | Lys | Glu | Arg | Leu | Val | Pro | Arg | Glu | Val | Pro | Arg | Arg | Val | |
| | | | | 200 | | | | | 205 | | | | | 210 | |

| ATC | AAC | GCC | ATC | AAC | ATC | AAC | CAT | GAG | TTC | GAC | CTG | CTG | GAT | GTG | 675 |
| Ile | Asn | Ala | Ile | Asn | Ile | Asn | His | Glu | Phe | Asp | Leu | Leu | Asp | Val | |
| | | | | 215 | | | | | 220 | | | | | 225 | |

| CGC | TTC | CAT | GAG | CTG | GGC | GAT | GTT | GTG | GAC | GCC | TTT | GTG | GTC | TGC | 720 |
| Arg | Phe | His | Glu | Leu | Gly | Asp | Val | Val | Asp | Ala | Phe | Val | Val | Cys | |
| | | | | 230 | | | | | 235 | | | | | 240 | |

| GAA | TCC | AAT | TTC | ACC | GCC | TAC | GGG | GAG | CCT | CGG | CCG | CTC | AAG | TTC | 765 |
| Glu | Ser | Asn | Phe | Thr | Ala | Tyr | Gly | Glu | Pro | Arg | Pro | Leu | Lys | Phe | |
| | | | | 245 | | | | | 250 | | | | | 255 | |

| CGA | GAG | ATG | CTG | ACC | AAT | GGC | ACC | TTC | GAG | TAC | ATC | CGC | CAC | AAG | 810 |
| Arg | Glu | Met | Leu | Thr | Asn | Gly | Thr | Phe | Glu | Tyr | Ile | Arg | His | Lys | |
| | | | | 260 | | | | | 265 | | | | | 270 | |

| GTG | CTC | TAC | GTC | TTC | CTG | GAC | CAC | TTC | CCA | CCT | GGT | GGC | CGT | CAG | 855 |
| Val | Leu | Tyr | Val | Phe | Leu | Asp | His | Phe | Pro | Pro | Gly | Gly | Arg | Gln | |
| | | | | 275 | | | | | 280 | | | | | 285 | |

| | | | | | | | | | | | | | | |
|---|---|---|---|---|---|---|---|---|---|---|---|---|---|---|
| GAC | GGC | TGG | ATT | GCA | GAC | GAC | TAC | CTG | CGT | ACC | TTC | CTC | ACC | CAG | 900
| Asp | Gly | Trp | Ile | Ala 290 | Asp | Asp | Tyr | Leu 295 | Arg | Thr | Phe | Leu | Thr | Gln 300 |
| GAT | GGT | GTC | TCC | CGC | CTG | CGC | AAC | CTG | CGA | CCT | GAT | GAC | GTC | TTT | 945
| Asp | Gly | Val | Ser | Arg 305 | Leu | Arg | Asn | Leu 310 | Arg | Pro | Asp | Asp | Val | Phe 315 |
| ATC | ATC | GAC | GAC | GCG | GAC | GAG | ATC | CCT | GCG | CGT | GAT | GGT | GTG | CTG | 990
| Ile | Ile | Asp | Asp | Ala 320 | Asp | Glu | Ile | Pro 325 | Ala | Arg | Asp | Gly | Val | Leu 330 |
| TTC | CTC | AAG | CTC | TAC | GAT | GGC | TGG | ACA | GAG | CCC | TTC | GCC | TTC | CAT | 1035
| Phe | Leu | Lys | Leu | Tyr 335 | Asp | Gly | Trp | Thr 340 | Glu | Pro | Phe | Ala | Phe | His 345 |
| ATG | CGC | AAG | TCC | CTG | TAT | GGT | TTC | TTT | TGG | AAG | CAA | CCA | GGC | ACA | 1080
| Met | Arg | Lys | Ser | Leu 350 | Tyr | Gly | Phe | Phe 355 | Trp | Lys | Gln | Pro | Gly | Thr 360 |
| CTG | GAG | GTG | GTG | TCA | GGC | TGC | ACC | ATT | GAC | ATG | CTG | CAG | GCT | GTG | 1125
| Leu | Glu | Val | Val | Ser 365 | Gly | Cys | Thr | Ile 370 | Asp | Met | Leu | Gln | Ala | Val 375 |
| TAT | GGG | CTG | GAC | GGC | ATC | CGC | CTG | CGC | CGC | CGT | CAG | TAC | TAC | ACC | 1170
| Tyr | Gly | Leu | Asp | Gly 380 | Ile | Arg | Leu | Arg 385 | Arg | Arg | Gln | Tyr | Tyr | Thr 390 |
| ATG | CCC | AAC | TTT | CGA | CAG | TAT | GAG | AAC | CGC | ACC | GGC | CAC | ATC | CTA | 1215
| Met | Pro | Asn | Phe | Arg 395 | Gln | Tyr | Glu | Asn 400 | Arg | Thr | Gly | His | Ile | Leu 405 |
| GTG | CAG | TGG | TCT | CTC | GGC | AGC | CCC | CTG | CAC | TTC | GCG | GGC | TGG | CAC | 1260
| Val | Gln | Trp | Ser | Leu 410 | Gly | Ser | Pro | Leu 415 | His | Phe | Ala | Gly | Trp | His 420 |
| TGC | TCC | TGG | TGC | TTC | ACA | CCC | GAG | GGC | ATC | TAC | TTC | AAA | CTC | GTG | 1305
| Cys | Ser | Trp | Cys | Phe 425 | Thr | Pro | Glu | Gly 430 | Ile | Tyr | Phe | Lys | Leu | Val 435 |
| TCG | GCC | CAG | AAT | GGT | GAC | TTC | CCC | CGC | TGG | GGT | GAC | TAC | GAG | GAC | 1350
| Ser | Ala | Gln | Asn | Gly 440 | Asp | Phe | Pro | Arg 445 | Trp | Gly | Asp | Tyr | Glu | Asp 450 |
| AAG | AGG | GAC | CTC | AAT | TAC | ATC | CGA | AGC | TTG | ATT | CGC | ACT | GGG | GGA | 1395
| Lys | Arg | Asp | Leu | Asn 455 | Tyr | Ile | Arg | Ser 460 | Leu | Ile | Arg | Thr | Gly | Gly 465 |
| TGG | TTC | GAC | GGC | ACG | CAG | CAG | GAG | TAC | CCT | CCT | GCA | GAC | CCC | AGT | 1440
| Trp | Phe | Asp | Gly | Thr 470 | Gln | Gln | Glu | Tyr 475 | Pro | Pro | Ala | Asp | Pro | Ser 480 |
| GAA | CAC | ATG | TAT | GCT | CCT | AAG | TAC | CTG | CTC | AAG | AAC | TAT | GAC | CAG | 1485
| Glu | His | Met | Tyr | Ala 485 | Pro | Lys | Tyr | Leu 490 | Leu | Lys | Asn | Tyr | Asp | Gln 495 |
| TTC | CGC | TAC | TTG | CTC | GAA | AAT | CCC | TAC | CGG | GAG | CCC | AAG | AGC | ACT | 1530
| Phe | Arg | Tyr | Leu | Leu 500 | Glu | Asn | Pro | Tyr 505 | Arg | Glu | Pro | Lys | Ser | Thr 510 |
| GTA | GAG | GGT | GGG | CGC | CGG | AAC | CAG | GGC | TCA | GAC | GGA | AGG | TCA | TCT | 1575
| Val | Glu | Gly | Gly | Arg 515 | Arg | Asn | Gln | Gly 520 | Ser | Asp | Gly | Arg | Ser | Ser 525 |
| GCT | GTC | AGG | GGC | AAG | TTG | GAT | ACA | ACG | GAG | GGC | | | | | 1608
| Ala | Val | Arg | Gly | Lys 530 | Leu | Asp | Thr | Thr | Glu 535 | Gly | | | | |

( 2 ) INFORMATION FOR SEQ ID NO:4:

( i ) SEQUENCE CHARACTERISTICS:
        ( A ) LENGTH: 531 amino acid residues
        ( B ) TYPE: amino acid
        ( C ) STRANDEDNESS:
        ( D ) TOPOLOGY: linear ( i i ) MOLECULE TYPE:

( x i ) SEQUENCE DESCRIPTION: SEQ ID NO:4:

| | | | | | | | | | | | | | | |
|---|---|---|---|---|---|---|---|---|---|---|---|---|---|---|
| Met | Arg | Arg | Tyr | Lys | Leu | Phe | Leu | Met | Phe | Cys | Met | Ala | Gly | Leu |
| 1 | | | | 5 | | | | | 10 | | | | | 15 |
| Cys | Leu | Ile | Ser | Phe | Leu | His | Phe | Phe | Lys | Thr | Leu | Ser | Tyr | Val |
| | | | | 20 | | | | | 25 | | | | | 30 |
| Thr | Phe | Pro | Arg | Glu | Leu | Ala | Ser | Leu | Ser | Pro | Asn | Leu | Val | Ser |
| | | | | 35 | | | | | 40 | | | | | 45 |
| Ser | Phe | Phe | Trp | Asn | Asn | Ala | Pro | Val | Thr | Pro | Gln | Ala | Ser | Pro |
| | | | | 50 | | | | | 55 | | | | | 60 |
| Glu | Pro | Gly | Gly | Pro | Asp | Leu | Leu | Arg | Thr | Pro | Leu | Tyr | Ser | His |
| | | | | 65 | | | | | 70 | | | | | 75 |
| Ser | Pro | Leu | Leu | Gln | Pro | Leu | Pro | Pro | Ser | Lys | Ala | Ala | Glu | Glu |
| | | | | 80 | | | | | 85 | | | | | 90 |
| Leu | His | Arg | Val | Asp | Leu | Val | Leu | Pro | Glu | Asp | Thr | Thr | Glu | Tyr |
| | | | | 95 | | | | | 100 | | | | | 105 |
| Phe | Val | Arg | Thr | Lys | Ala | Gly | Gly | Val | Cys | Phe | Lys | Pro | Gly | Thr |
| | | | | 110 | | | | | 115 | | | | | 120 |
| Lys | Met | Leu | Glu | Arg | Pro | Pro | Pro | Gly | Arg | Pro | Glu | Glu | Lys | Pro |
| | | | | 125 | | | | | 130 | | | | | 135 |
| Glu | Gly | Ala | Asn | Gly | Ser | Ser | Ala | Arg | Arg | Pro | Pro | Arg | Tyr | Leu |
| | | | | 140 | | | | | 145 | | | | | 150 |
| Leu | Ser | Ala | Arg | Glu | Arg | Thr | Gly | Gly | Arg | Gly | Ala | Arg | Arg | Lys |
| | | | | 155 | | | | | 160 | | | | | 165 |
| Trp | Val | Glu | Cys | Val | Cys | Leu | Pro | Gly | Trp | His | Gly | Pro | Ser | Cys |
| | | | | 170 | | | | | 175 | | | | | 180 |
| Gly | Val | Pro | Thr | Val | Val | Gln | Tyr | Ser | Asn | Leu | Pro | Thr | Lys | Glu |
| | | | | 185 | | | | | 190 | | | | | 195 |
| Arg | Leu | Val | Pro | Arg | Glu | Val | Pro | Arg | Arg | Val | Ile | Asn | Ala | Ile |
| | | | | 200 | | | | | 205 | | | | | 210 |
| Asn | Val | Asn | His | Glu | Phe | Asp | Leu | Leu | Asp | Val | Arg | Phe | His | Glu |
| | | | | 215 | | | | | 220 | | | | | 225 |
| Leu | Gly | Asp | Val | Val | Asp | Ala | Phe | Val | Val | Cys | Glu | Ser | Asn | Phe |
| | | | | 230 | | | | | 235 | | | | | 240 |
| Thr | Ala | Tyr | Gly | Glu | Pro | Arg | Pro | Leu | Lys | Phe | Arg | Glu | Met | Leu |
| | | | | 245 | | | | | 250 | | | | | 255 |
| Thr | Asn | Gly | Thr | Phe | Glu | Tyr | Ile | Arg | His | Lys | Val | Leu | Tyr | Val |
| | | | | 260 | | | | | 265 | | | | | 270 |
| Phe | Leu | Asp | His | Phe | Pro | Pro | Gly | Gly | Arg | Gln | Asp | Gly | Trp | Ile |
| | | | | 275 | | | | | 280 | | | | | 285 |
| Ala | Asp | Asp | Tyr | Leu | Arg | Thr | Phe | Leu | Thr | Gln | Asp | Gly | Val | Ser |
| | | | | 290 | | | | | 295 | | | | | 300 |
| Arg | Leu | Arg | Asn | Leu | Arg | Pro | Asp | Asp | Val | Phe | Ile | Ile | Asp | Asp |
| | | | | 305 | | | | | 310 | | | | | 315 |
| Ala | Asp | Glu | Ile | Pro | Ala | Arg | Asp | Gly | Val | Leu | Phe | Leu | Lys | Leu |
| | | | | 320 | | | | | 325 | | | | | 330 |
| Tyr | Asp | Gly | Trp | Thr | Glu | Pro | Phe | Ala | Phe | His | Met | Arg | Thr | Ser |
| | | | | 335 | | | | | 340 | | | | | 345 |
| Leu | Tyr | Gly | Phe | Phe | Trp | Lys | Gln | Pro | Gly | Thr | Leu | Glu | Val | Val |
| | | | | 350 | | | | | 355 | | | | | 360 |
| Ser | Gly | Cys | Thr | Val | Asp | Met | Leu | Gln | Ala | Val | Tyr | Gly | Leu | Asp |
| | | | | 365 | | | | | 370 | | | | | 375 |
| Gly | Ile | Arg | Leu | Arg | Arg | Arg | Gln | Tyr | Tyr | Thr | Met | Pro | Asn | Phe |
| | | | | 380 | | | | | 385 | | | | | 390 |
| Arg | Gln | Tyr | Glu | Asn | Arg | Thr | Gly | His | Ile | Leu | Val | Gln | Trp | Ser |

|     |     |     |     | 395 |     |     |     |     | 400 |     |     |     |     | 405 |
| --- | --- | --- | --- | --- | --- | --- | --- | --- | --- | --- | --- | --- | --- | --- |
| Leu | Gly | Ser | Pro | Leu | His | Phe | Ala | Gly | Trp | His | Cys | Ser | Trp | Cys |
|     |     |     |     | 410 |     |     |     |     | 415 |     |     |     |     | 420 |
| Phe | Thr | Pro | Glu | Gly | Ile | Tyr | Phe | Lys | Leu | Val | Ser | Ala | Gln | Asn |
|     |     |     |     | 425 |     |     |     |     | 430 |     |     |     |     | 435 |
| Gly | Asp | Phe | Pro | Arg | Trp | Gly | Asp | Tyr | Glu | Asp | Lys | Arg | Asp | Leu |
|     |     |     |     | 440 |     |     |     |     | 445 |     |     |     |     | 450 |
| Asn | Tyr | Ile | Arg | Gly | Leu | Ile | Arg | Thr | Gly | Gly | Trp | Phe | Asp | Gly |
|     |     |     |     | 455 |     |     |     |     | 460 |     |     |     |     | 465 |
| Thr | Gln | Gln | Glu | Tyr | Pro | Pro | Ala | Asp | Pro | Ser | Glu | His | Met | Tyr |
|     |     |     |     | 470 |     |     |     |     | 475 |     |     |     |     | 480 |
| Ala | Pro | Lys | Tyr | Leu | Leu | Lys | Asn | Tyr | Asp | Arg | Phe | His | Tyr | Leu |
|     |     |     |     | 485 |     |     |     |     | 490 |     |     |     |     | 495 |
| Leu | Asp | Asn | Pro | Tyr | Gln | Glu | Pro | Arg | Ser | Thr | Ala | Ala | Gly | Gly |
|     |     |     |     | 500 |     |     |     |     | 505 |     |     |     |     | 510 |
| Trp | Arg | His | Arg | Gly | Pro | Gly | Arg | Pro | Pro | Ala | Arg | Gly | Lys |     |
|     |     |     |     | 515 |     |     |     |     | 520 |     |     |     |     | 525 |
| Leu | Asp | Glu | Ala | Glu | Val |     |     |     |     |     |     |     |     |     |
|     |     |     |     | 530 |     |     |     |     |     |     |     |     |     |     |

( 2 ) INFORMATION FOR SEQ ID NO:5:

( i ) SEQUENCE CHARACTERISTICS:
        ( A ) LENGTH: 536 amino acid residues
        ( B ) TYPE: amino acid
        ( C ) STRANDEDNESS:
        ( D ) TOPOLOGY: linear ( i i ) MOLECULE TYPE:

( i x ) SEQUENCE DESCRIPTION: SEQ ID NO: 5:

|     |     |     |     |     |     |     |     |     |     |     |     |     |     |     |
| --- | --- | --- | --- | --- | --- | --- | --- | --- | --- | --- | --- | --- | --- | --- |
| Met | Arg | Arg | Tyr | Lys | Leu | Phe | Leu | Met | Phe | Cys | Met | Ala | Gly | Leu |
| 1   |     |     |     | 5   |     |     |     |     | 10  |     |     |     |     | 15  |
| Cys | Leu | Ile | Ser | Phe | Leu | His | Phe | Phe | Lys | Thr | Leu | Ser | Tyr | Val |
|     |     |     |     | 20  |     |     |     |     | 25  |     |     |     |     | 30  |
| Thr | Phe | Pro | Arg | Glu | Leu | Ala | Ser | Leu | Ser | Pro | Asn | Leu | Ile | Ser |
|     |     |     |     | 35  |     |     |     |     | 40  |     |     |     |     | 45  |
| Ser | Phe | Phe | Trp | Asn | Asn | Ala | Pro | Val | Thr | Pro | Gln | Ala | Ser | Pro |
|     |     |     |     | 50  |     |     |     |     | 55  |     |     |     |     | 60  |
| Glu | Pro | Gly | Asp | Pro | Asp | Leu | Leu | Arg | Thr | Pro | Leu | Tyr | Ser | His |
|     |     |     |     | 65  |     |     |     |     | 70  |     |     |     |     | 75  |
| Ser | Pro | Leu | Leu | Gln | Pro | Leu | Ser | Pro | Ser | Lys | Ala | Thr | Glu | Glu |
|     |     |     |     | 80  |     |     |     |     | 85  |     |     |     |     | 90  |
| Leu | His | Arg | Val | Asp | Phe | Val | Leu | Pro | Glu | Asp | Thr | Thr | Glu | Tyr |
|     |     |     |     | 95  |     |     |     |     | 100 |     |     |     |     | 105 |
| Phe | Val | Arg | Thr | Lys | Ala | Gly | Gly | Val | Cys | Phe | Lys | Pro | Gly | Thr |
|     |     |     |     | 110 |     |     |     |     | 115 |     |     |     |     | 120 |
| Arg | Met | Leu | Glu | Lys | Pro | Ser | Pro | Gly | Arg | Thr | Glu | Glu | Lys | Thr |
|     |     |     |     | 125 |     |     |     |     | 130 |     |     |     |     | 135 |
| Lys | Val | Ala | Glu | Gly | Ser | Ser | Val | Arg | Gly | Pro | Ala | Arg | Arg | Pro |
|     |     |     |     | 140 |     |     |     |     | 145 |     |     |     |     | 150 |
| Met | Arg | His | Val | Leu | Ser | Ala | Arg | Glu | Arg | Leu | Gly | Gly | Arg | Gly |
|     |     |     |     | 155 |     |     |     |     | 160 |     |     |     |     | 165 |
| Thr | Arg | Arg | Lys | Trp | Val | Glu | Cys | Val | Cys | Leu | Pro | Gly | Trp | His |
|     |     |     |     | 170 |     |     |     |     | 175 |     |     |     |     | 180 |
| Gly | Pro | Ser | Cys | Gly | Val | Pro | Thr | Val | Val | Gln | Tyr | Ser | Asn | Leu |
|     |     |     |     | 185 |     |     |     |     | 190 |     |     |     |     | 195 |

-continued

| | | | | | | | | | | | | | |
|---|---|---|---|---|---|---|---|---|---|---|---|---|---|
| Pro | Thr | Lys | Glu | Arg 200 | Leu | Val | Pro | Arg 205 | Val | Pro | Arg | Arg | Val 210 |
| Ile | Asn | Ala | Ile | Asn 215 | Ile | Asn | His | Glu | Phe 220 | Asp | Leu | Leu | Asp Val 225 |
| Arg | Phe | His | Glu | Leu 230 | Gly | Asp | Val | Val | Asp 235 | Ala | Phe | Val | Val Cys 240 |
| Glu | Ser | Asn | Phe | Thr 245 | Ala | Tyr | Gly | Glu | Pro 250 | Arg | Pro | Leu | Lys Phe 255 |
| Arg | Glu | Met | Leu | Thr 260 | Asn | Gly | Thr | Phe | Glu 265 | Tyr | Ile | Arg | His Lys 270 |
| Val | Leu | Tyr | Val | Phe 275 | Leu | Asp | His | Phe | Pro 280 | Pro | Gly | Gly | Arg Gln 285 |
| Asp | Gly | Trp | Ile | Ala 290 | Asp | Asp | Tyr | Leu | Arg 295 | Thr | Phe | Leu | Thr Gln 300 |
| Asp | Gly | Val | Ser | Arg 305 | Leu | Arg | Asn | Leu | Arg 310 | Pro | Asp | Asp | Val Phe 315 |
| Ile | Ile | Asp | Asp | Ala 320 | Asp | Glu | Ile | Pro | Ala 325 | Arg | Asp | Gly | Val Leu 330 |
| Phe | Leu | Lys | Leu | Tyr 335 | Asp | Gly | Trp | Thr | Glu 340 | Pro | Phe | Ala | Phe His 345 |
| Met | Arg | Lys | Ser | Leu 350 | Tyr | Gly | Phe | Phe | Trp 355 | Lys | Gln | Pro | Gly Thr 360 |
| Leu | Glu | Val | Val | Ser 365 | Gly | Cys | Thr | Ile | Asp 370 | Met | Leu | Gln | Ala Val 375 |
| Tyr | Gly | Leu | Asp | Gly 380 | Ile | Arg | Leu | Arg | Arg 385 | Arg | Gln | Tyr | Tyr Thr 390 |
| Met | Pro | Asn | Phe | Arg 395 | Gln | Tyr | Glu | Asn | Arg 400 | Thr | Gly | His | Ile Leu 405 |
| Val | Gln | Trp | Ser | Leu 410 | Gly | Ser | Pro | Leu | His 415 | Phe | Ala | Gly | Trp His 420 |
| Cys | Ser | Trp | Cys | Phe 425 | Thr | Pro | Glu | Gly | Ile 430 | Tyr | Phe | Lys | Leu Val 435 |
| Ser | Ala | Gln | Asn | Gly 440 | Asp | Phe | Pro | Arg | Trp 445 | Gly | Asp | Tyr | Glu Asp 450 |
| Lys | Arg | Asp | Leu | Asn 455 | Tyr | Ile | Arg | Ser | Leu 460 | Ile | Arg | Thr | Gly Gly 465 |
| Trp | Phe | Asp | Gly | Thr 470 | Gln | Gln | Glu | Tyr | Pro 475 | Pro | Ala | Asp | Pro Ser 480 |
| Glu | His | Met | Tyr | Ala 485 | Pro | Lys | Tyr | Leu | Leu 490 | Lys | Asn | Tyr | Asp Gln 495 |
| Phe | Arg | Tyr | Leu | Leu 500 | Glu | Asn | Pro | Tyr | Arg 505 | Glu | Pro | Lys | Ser Thr 510 |
| Val | Glu | Gly | Gly | Arg 515 | Arg | Asn | Gln | Gly | Ser 520 | Asp | Gly | Arg | Ser Ser 525 |
| Ala | Val | Arg | Gly | Lys 530 | Leu | Asp | Thr | Thr | Glu 535 | Gly | | | |